(12) United States Patent
Bate et al.

(10) Patent No.: US 7,902,428 B2
(45) Date of Patent: Mar. 8, 2011

(54) PLANT REGULATORY REGION THAT DIRECTS TRANSGENE EXPRESSION IN THE MATERNAL AND SUPPORTING TISSUE OF MAIZE OVULES AND POLLINATED KERNELS

(75) Inventors: Nicholas J Bate, Urbandale, IA (US); Kellie Reimann, Ankeny, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 12/186,609

(22) Filed: Aug. 6, 2008

(65) Prior Publication Data

US 2009/0094713 A1    Apr. 9, 2009

Related U.S. Application Data

(60) Provisional application No. 60/963,878, filed on Aug. 7, 2007.

(51) Int. Cl.
*A01H 5/00* (2006.01)
*C12N 5/14* (2006.01)
*C12N 15/63* (2006.01)
*C07H 21/04* (2006.01)

(52) U.S. Cl. ...... 800/295; 800/298; 800/320; 800/320.1; 435/320.1; 435/419; 536/24.1

(58) Field of Classification Search ................. None
See application file for complete search history.

(56) References Cited

U.S. PATENT DOCUMENTS

| 5,986,174 | A | * | 11/1999 | Barbour et al. | ............... 800/287 |
| 2007/0209085 | A1 | * | 9/2007 | Wu et al. | ...................... 800/278 |

OTHER PUBLICATIONS

Kim et al. (Plant Molecular Biology, 24:105-117, 1994).*
Benfey et al. (Science 250:959-966, 1990).*
Sun, Y., et al.; "Inositol 1,3,4,5,6-Pentakisphosphate 2-Kinase from Maize: Molecular and Biochemical Characterization"; Plant Physiology (Jul. 2007) 144:1278-1291; American Society of Plant Biologists; Rockville, MD, US.
Wilson, R.K., et al.; "The sequence of *Zea mays* bac clone CH201-522E3"; EBL Database Accession No. AC200197; Mar. 2007.

* cited by examiner

*Primary Examiner* — Vinod Kumar

(57) ABSTRACT

Compositions and methods for regulating expression of heterologous nucleotide sequences in a plant are provided. Compositions include a novel nucleotide sequence for a maize actin depolymerization factor 4 promoter. Also provided is a method for expressing a heterologous nucleotide sequence in a plant using a promoter sequence disclosed herein.

14 Claims, 12 Drawing Sheets
(12 of 12 Drawing Sheet(s) Filed in Color)

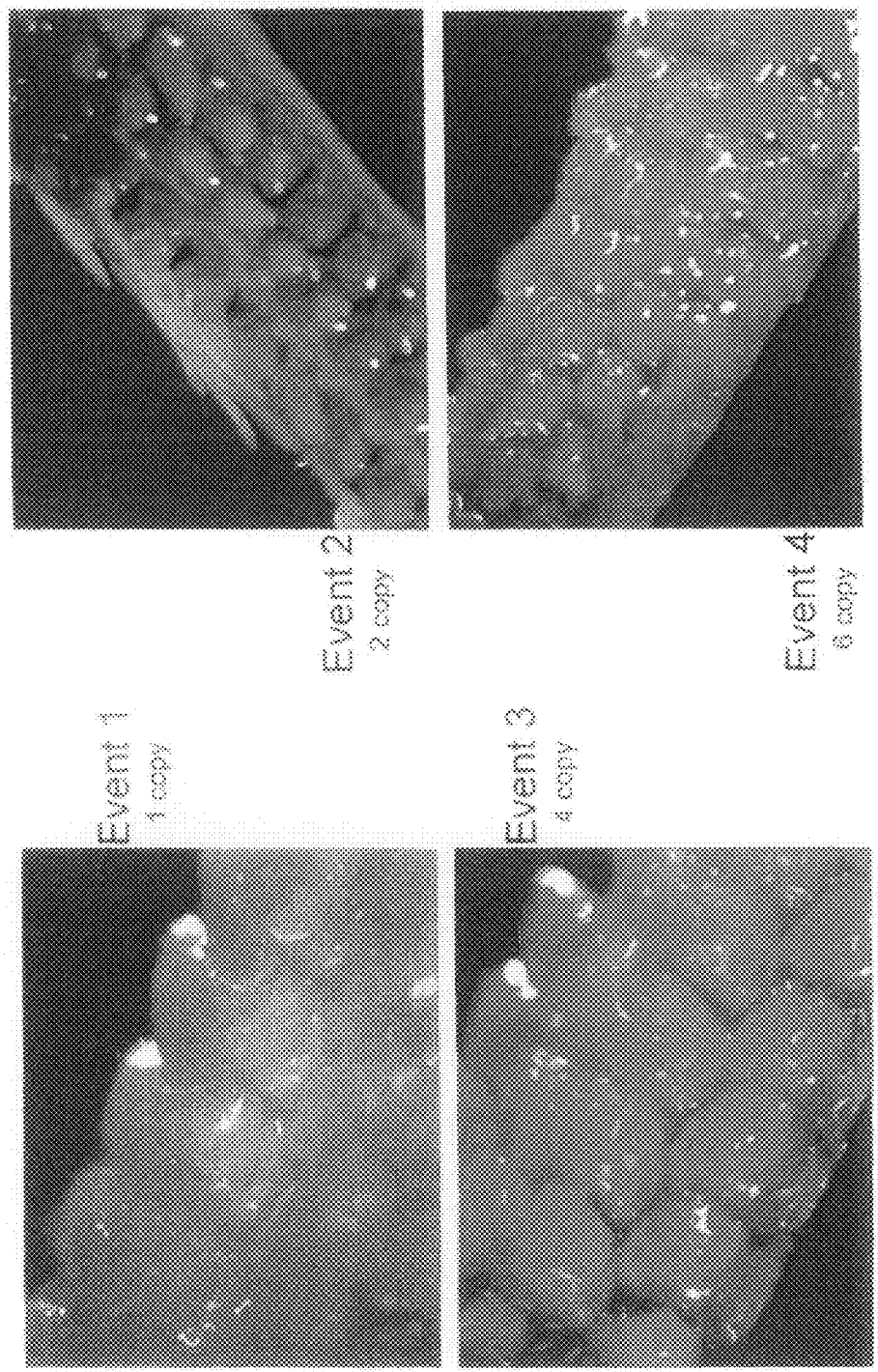

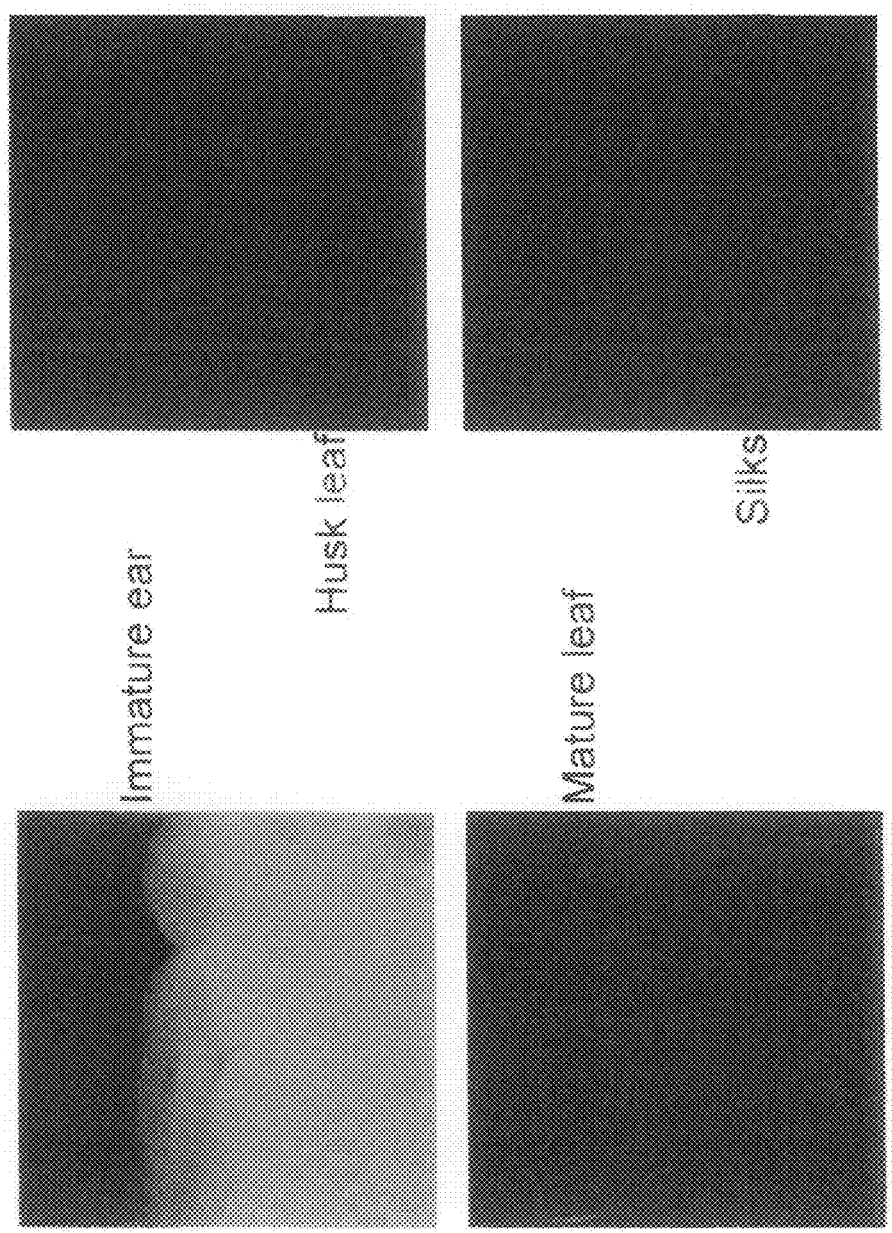

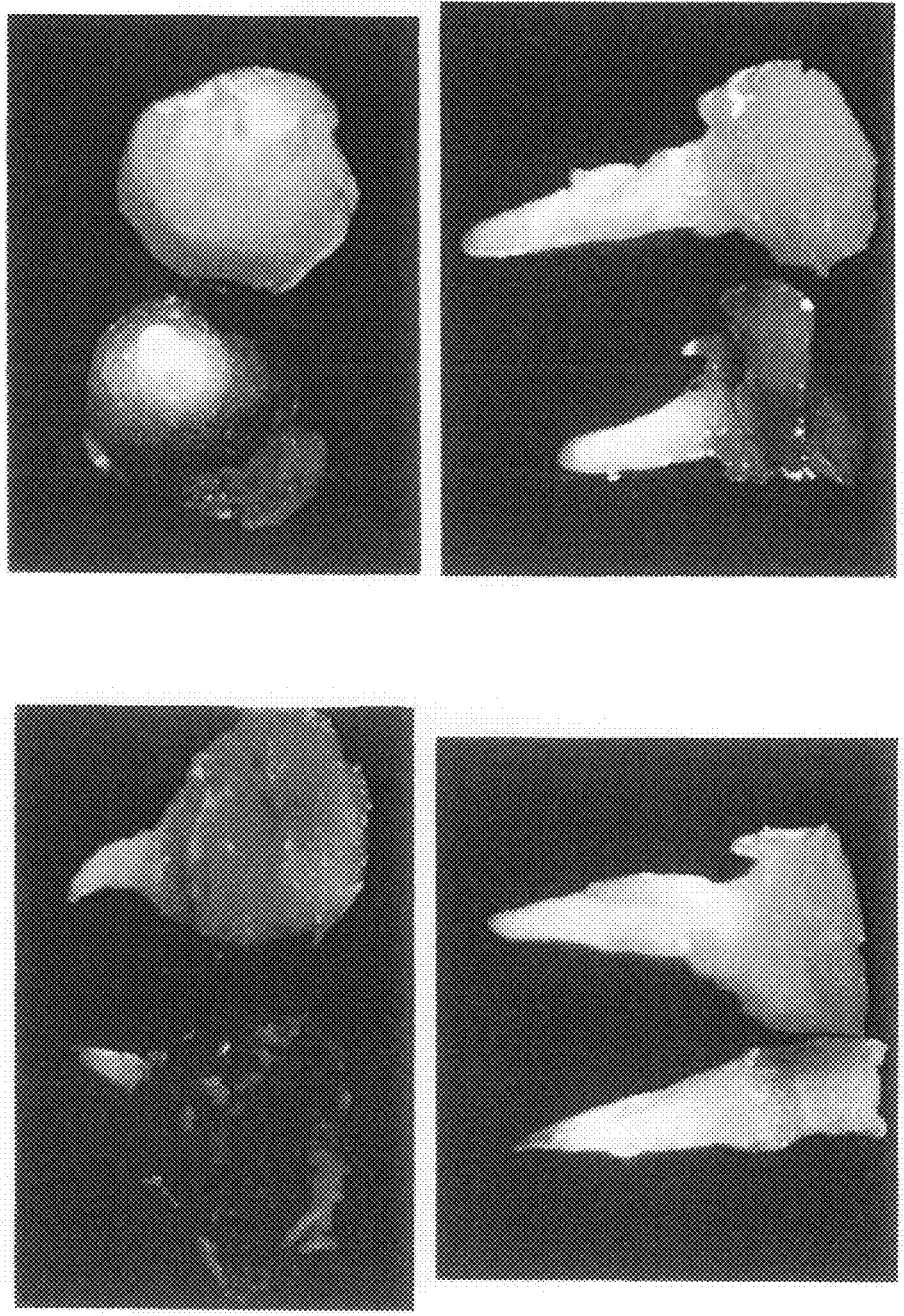

Figure 5:
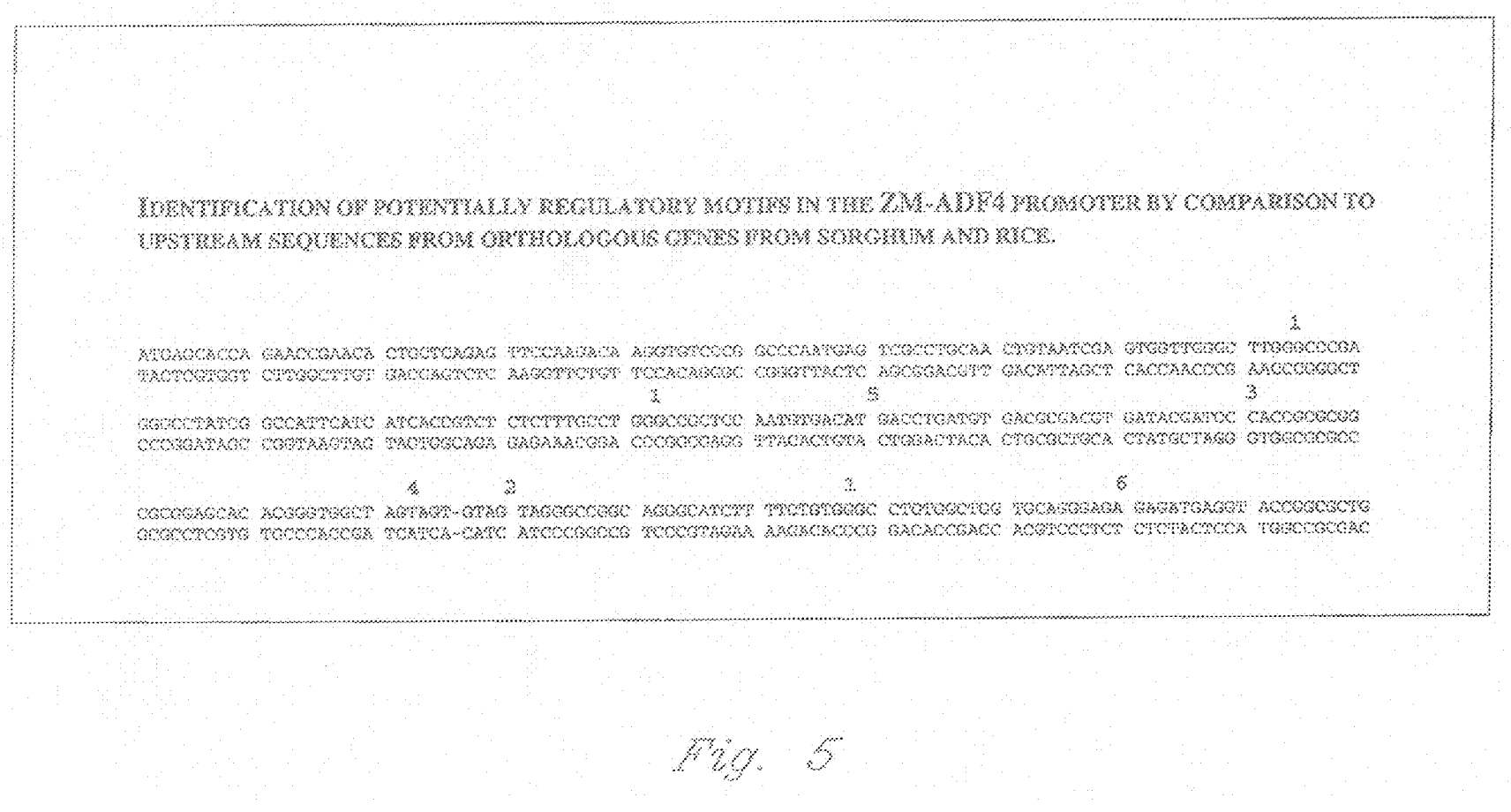

IDENTIFICATION OF POTENTIALLY REGULATORY MOTIFS IN THE ZM-ADF4 PROMOTER BY COMPARISON TO UPSTREAM SEQUENCES FROM ORTHOLOGOUS GENES FROM SORGHUM AND RICE.

SEQUENCE LISTING

<160> NUMBER OF SEQ ID NOS: 8

<210> SEQ ID NO 1
<211> LENGTH: 1390
<212> TYPE: DNA
<213> ORGANISM: Zea mays
<220> FEATURE:
<221> NAME/KEY: promoter
<222> LOCATION: (7)...(1026)
<223> OTHER INFORMATION: upstream regulatory region from maize ADF4 gene
<220> FEATURE:
<221> NAME/KEY: 5'UTR
<222> LOCATION: (1027)...(1147)
<223> OTHER INFORMATION: untranslated leader of maize ADF4 gene
<220> FEATURE:
<221> NAME/KEY: intron
<222> LOCATION: (1151)...(1319)
<223> OTHER INFORMATION: first intron from maize ADF4; from genomic B73
<220> FEATURE:
<221> NAME/KEY: CDS
<222> LOCATION: (1338)...(1385)
<223> OTHER INFORMATION: coding sequence from maize ADF4 amplified from genomic B73

<400> SEQUENCE: 1

```
aagcttgagt gttgtcgtgt tgctcgattg ctaacaccct ccctcctcga acagcgcccg      60
acatctctta aggtagtgtt tggttctgga gttaggtggg gtggagccgt tccattctac     120
tttttgtgtt gttgagttgt attccggttg aagcagagtg gctcaaattc tagaatatac     180
ccttgagatg cggcatcccg tggctcctca aaattaatcg gatttggctg ctcgtgagcc     240
gagcctccca ttcccatccc atctcttccc tgatgctcga cataagctca cccaagtttg     300
tttcaatttt cttctataga taaattactt ggggcagttt agaatttgca cgttgtttat     360
gtgagactac gtctattagc tatttcttaa ttataaaact caatgcctac tgatatgtat     420
gatataagta tgttttttatt gatcattgag ttaacatatg agaaacgaaa aaaatatac     480
tctattttgt atttatcaac caaatattag atgaagtcat tgtaaaatta aattatcaaa     540
catagaacag agtgactttg ttatcaaaat ctataatgga gccatttcat ctaaatgagc     600
accagaaccg aacactgctc agagttccaa gacaaggtgt cccggcccaa tgagtcgcct     660
gcaactgtaa tcgagtggtt gggcttgggc ccgagggcct atcggccatt catcatcacc     720
```

```
gtctctcttt gcctgggccg ctccaatgtg acatgacctg atgtgacgcg acgtgatacg    780
atcccaccgc gcggcgcgga gcacacgggt ggctagtagt gtagtagggc cggcagggca    840
tcttttctgt gggcctgtgg ctggtgcagg gagagagatg aggtaccggc gctgagtcgc    900
tgacgggtgg ggcccgggtc ggtgccgaag gaggggggtgg ggtggtggcg cgtccatccc    960
acgcgactct cccacacaaa taccatcacc ttcgctacca ttgcttcacc atcaccacca   1020
ccccgcggct gcagctcagc agctccagac ctcaccagag gcacctacca caccgcccgc   1080
cgccgatccc gtcacccgtc tcctccccgc tgcggagcgt ctccagccct gcccggtgcc   1140
cgcccagatg gtaagcacgc ggcaccacac ttcacctcca gtcctgttca tcggctatgc   1200
gatctgcatt ttcgtttgct cgatcgacgg atctgccatg ctcttcttct tcacctccct   1260
cgtcttcgtc tccactgcct ctgaatcttg tttcgcctcc tctcccccgg gttctgcagg   1320
caaacgcggc gtcagggatg gccgtggacg acgactgcaa gcgccggttc ctggagctca   1380
aggccatgga                                                          1390

<210> SEQ ID NO 2
<211> LENGTH: 26
<212> TYPE: DNA
<213> ORGANISM: Artificial Sequence
<220> FEATURE:
<223> OTHER INFORMATION: primer

<400> SEQUENCE: 2
aagcttgagt gttgtcgtgt tgctcg                                          26

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
ccatggcctt gagctccagg aacc                                            24

<210> SEQ ID NO 4
<211> LENGTH: 300
<212> TYPE: DNA
<213> ORGANISM: Zea mays

<400> SEQUENCE: 4
atgagcacca gaaccgaaca ctgctcagag ttcaagacaa aggtgtcccg gcccaatgag     60
tcgcctgcaa ctgtaatcga gtggttgggc ttgggcccga gggcctatcg gccattcatc    120
atcaccgtct ctctttgcct gggccgctcc aatgtgacat gacctgatgt gacgcgacgt    180
gatacgatcc caccgcgcgg cgcggagcac acgggtggct agtagtgtag tagggccggc    240
agggcatctt tttctgtgggc ctgtggctgg tgcagggaga gagatgaggt accggcgctg    300

<210> SEQ ID NO 5
<211> LENGTH: 28
<212> TYPE: DNA
<213> ORGANISM: Unknown
<220> FEATURE:
<223> OTHER INFORMATION: meristematic tissue-specific element

<400> SEQUENCE: 5
cgaggtgggc ccgtaggtgg gcccgtat                                        28

<210> SEQ ID NO 6
```

```
<211> LENGTH: 24
<212> TYPE: DNA
<213> ORGANISM: Phaseolus vulgaris

<400> SEQUENCE: 6
ataatgggcc acactgtggg gcat                                               24

<210> SEQ ID NO 7
<211> LENGTH: 11
<212> TYPE: DNA
<213> ORGANISM: Unknown
<220> FEATURE:
<223> OTHER INFORMATION: part of a light responsive element

<400> SEQUENCE: 7
atcccaccta c                                                             11

<210> SEQ ID NO 8
<211> LENGTH: 21
<212> TYPE: DNA
<213> ORGANISM: Unknown
<220> FEATURE:
<223> OTHER INFORMATION: seed storage protein, napA

<400> SEQUENCE: 8
gatcccacat acacatacac g                                                  21
```

PLANT REGULATORY REGION THAT DIRECTS TRANSGENE EXPRESSION IN THE MATERNAL AND SUPPORTING TISSUE OF MAIZE OVULES AND POLLINATED KERNELS

CROSS REFERENCE

This utility application claims the benefit U.S. Provisional Application No. 60/963,878, filed Aug. 7, 2007, which is incorporated herein by reference.

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of operably linked regulatory elements that are functional within the plant host. Choice of the promoter sequence will determine when and where within the organism the heterologous DNA sequence is expressed. Where expression in specific tissues or organs is desired, tissue-preferred promoters may be used. Where gene expression in response to a stimulus is desired, inducible promoters are the regulatory element of choice. In contrast, where continuous expression is desired throughout the cells of a plant, constitutive promoters are utilized. Additional regulatory sequences upstream and/or downstream from the core promoter sequence may be included in the expression constructs of transformation vectors to bring about varying levels of expression of heterologous nucleotide sequences in a transgenic plant.

Frequently it is desirable to express a DNA sequence in particular tissues or organs of a plant. For example, increased resistance of a plant to infection by soil- and air-borne pathogens might be accomplished by genetic manipulation of the plant's genome to comprise a tissue-preferred promoter operably linked to a heterologous pathogen-resistance gene such that pathogen-resistance proteins are produced in the desired plant tissue. Alternatively, it might be desirable to inhibit expression of a native DNA sequence within a plant's tissues to achieve a desired phenotype. In this case, such inhibition might be accomplished with transformation of the plant to comprise a tissue-preferred promoter operably linked to an antisense nucleotide sequence, such that expression of the antisense sequence produces an RNA transcript that interferes with translation of the mRNA of the native DNA sequence.

Additionally, it may be desirable to express a DNA sequence in plant tissues that are in a particular growth or developmental phase such as, for example, cell division or elongation. Such a DNA sequence may be used to promote or inhibit plant growth processes, thereby affecting the growth rate or architecture of the plant.

Isolation and characterization of reproductive-tissue-preferred, particularly immature-ear-preferred, promoters that can serve as regulatory elements for expression of isolated nucleotide sequences of interest in a reproductive-tissue-preferred manner are needed for impacting various traits in plants and in use with scorable markers.

BRIEF SUMMARY OF THE INVENTION

Compositions and methods for regulating gene expression in a plant are provided. Compositions comprise novel nucleotide sequences for a reproductive-tissue-preferred promoter. More particularly, a transcriptional initiation region of the actin depolymerization factor 4 gene is provided. Further embodiments of the invention comprise the nucleotide sequence set forth in SEQ ID NO: 1 and fragments of the nucleotide sequence set forth in SEQ ID NO: 1. Also included are functional fragments of the sequence set forth as SEQ ID NO: 1 which drive reproductive-tissue-preferred expression of an operably linked nucleotide sequence.

Embodiments of the invention also include DNA constructs comprising a promoter operably linked to a heterologous nucleotide sequence of interest wherein said promoter is capable of driving expression of said nucleotide sequence in a plant cell and said promoter comprises one of the nucleotide sequences disclosed herein. Embodiments of the invention further provide expression vectors, and plants or plant cells having stably incorporated into their genomes a DNA construct mentioned above. Additionally, compositions include transgenic seed of such plants.

Further embodiments comprise a means for selectively expressing a nucleotide sequence in a plant, comprising transforming a plant cell with a DNA construct, and regenerating a transformed plant from said plant cell, said DNA construct comprising a promoter and a heterologous nucleotide sequence operably linked to said promoter, wherein said promoter initiates immature-ear-preferred transcription of said nucleotide sequence in a plant cell. In this manner, the promoter sequences are useful for controlling the expression of operably linked coding sequences in a tissue-preferred or inducible manner.

Downstream from the transcriptional initiation regulation of the promoter will be a sequence of interest that will provide for modification of the phenotype of the plant. Such modification includes modulating the production of an endogenous product, as to amount, relative distribution, or the like, or production of an exogenous expression product to provide for a novel function or product in the plant. For example, a heterologous nucleotide sequence that encodes a gene product that confers resistance or tolerance to herbicide, salt, cold, drought, pathogen, nematodes or insects is encompassed.

In a further embodiment, a method for modulating expression of a gene in a stably transformed plant is provided, comprising the steps of (a) transforming a plant cell with a DNA construct comprising the promoter of the embodiments operably linked to at least one nucleotide sequence; (b) growing the plant cell under plant growing conditions and (c) regenerating a stably transformed plant from the plant cell wherein expression of the nucleotide sequence alters the phenotype of the plant.

BRIEF DESCRIPTION OF THE DRAWINGS

This patent or application file contains at least one drawing figure executed in color. Copies of this patent or patent application publication with color drawing(s) will be provided by the Office upon request and payment of the necessary fee.

FIG. 2 shows photographs of the transgenic expression of the GUS scorable marker when operatively linked to the ADF4 promoter and expressed in T0 transgenic plants.

FIG. 3 shows photographs of the transgenic expression of the DS-RED scorable marker when operatively linked to the ADF4 promoter and expressed in T0 transgenic plants.

FIGS. 4A-4H show photographs of the transgenic expression of the DS-RED and GUS scorable markers when operatively linked to the ADF4 promoter and expressed in T1 transgenic plants. For comparative purposes, tissue from a control plant is shown on the right in each panel of 4A; on the right in the final two panels of 4B; as marked in 4C; in the lower ear and upper anther of 4D; in the lower ears or right ear cross-section of 4E; and as indicated in 4F.

FIG. 5 is a 300 base pair region of the ADF4-promoter (SEQ ID NO: 4) showing the location of motifs by comparison to orthologous genes from sorghum and rice as described in Tables 1-3 and Example 4.

Figure 1:
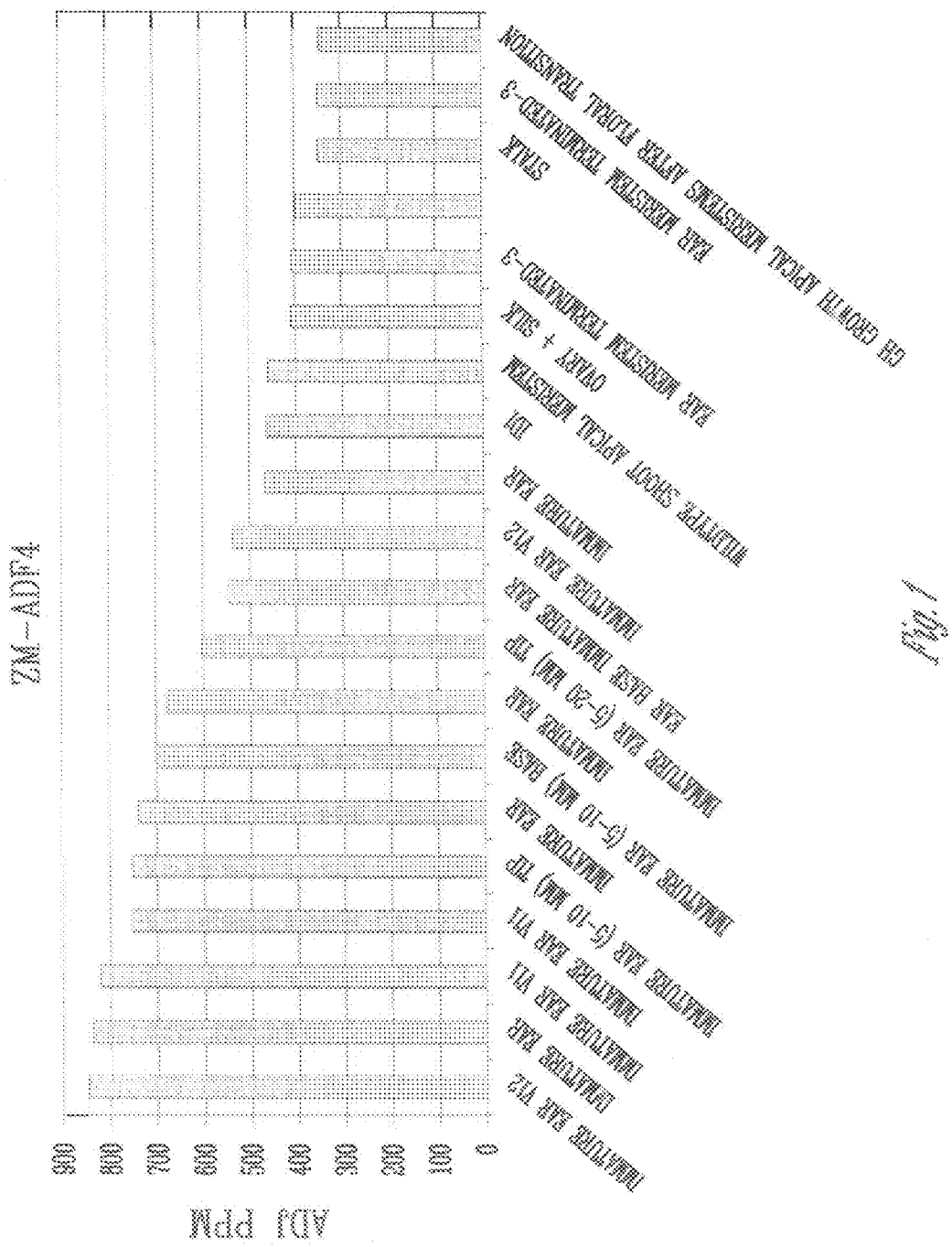
FIG. 1 shows the summary of LYNX™ Massively Parallel Signature Sequencing data illustrating the expression of ADF4 in *zea mays*.
Figure 4B:
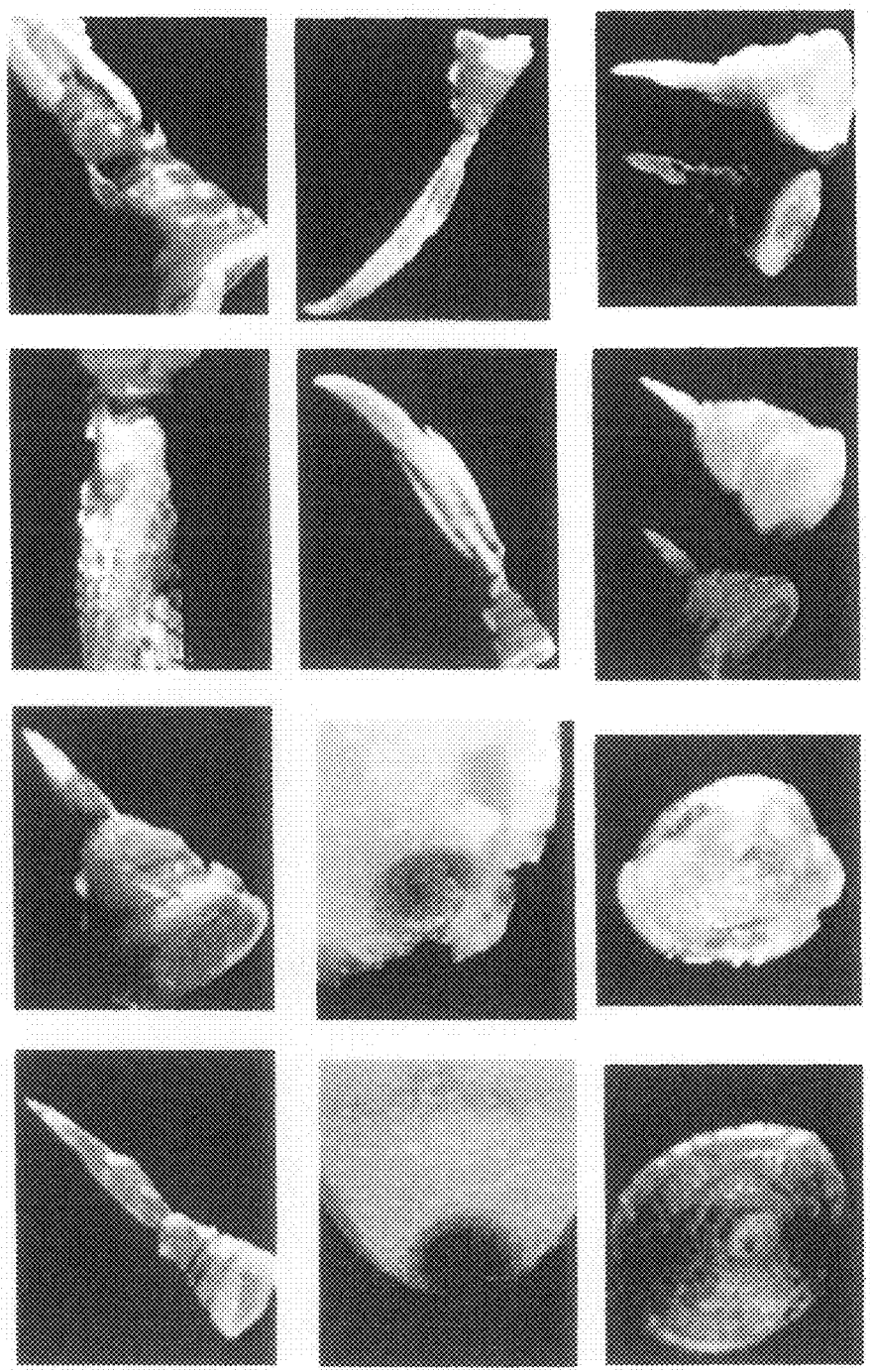
Figure 4C:
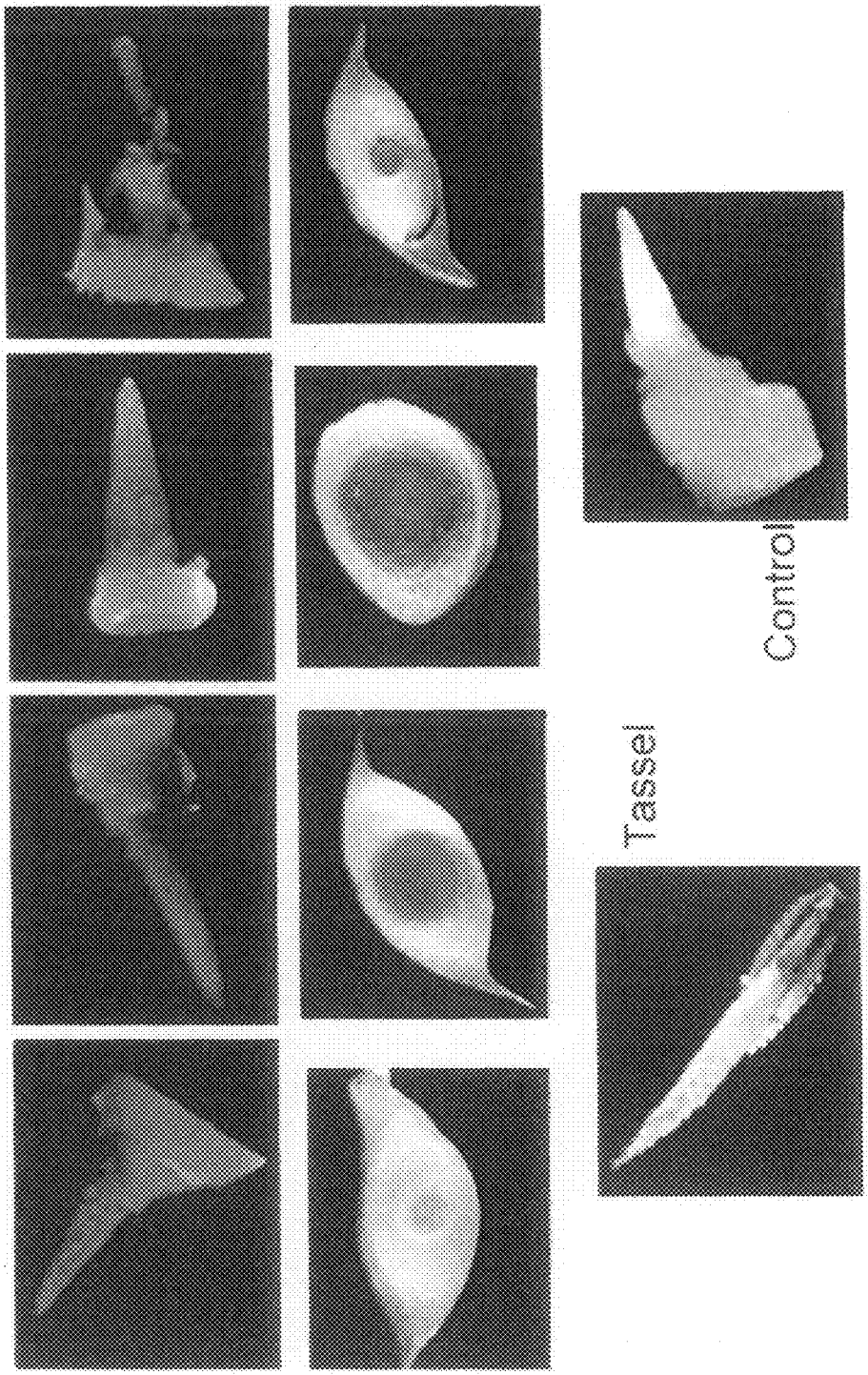
Figure 4D:
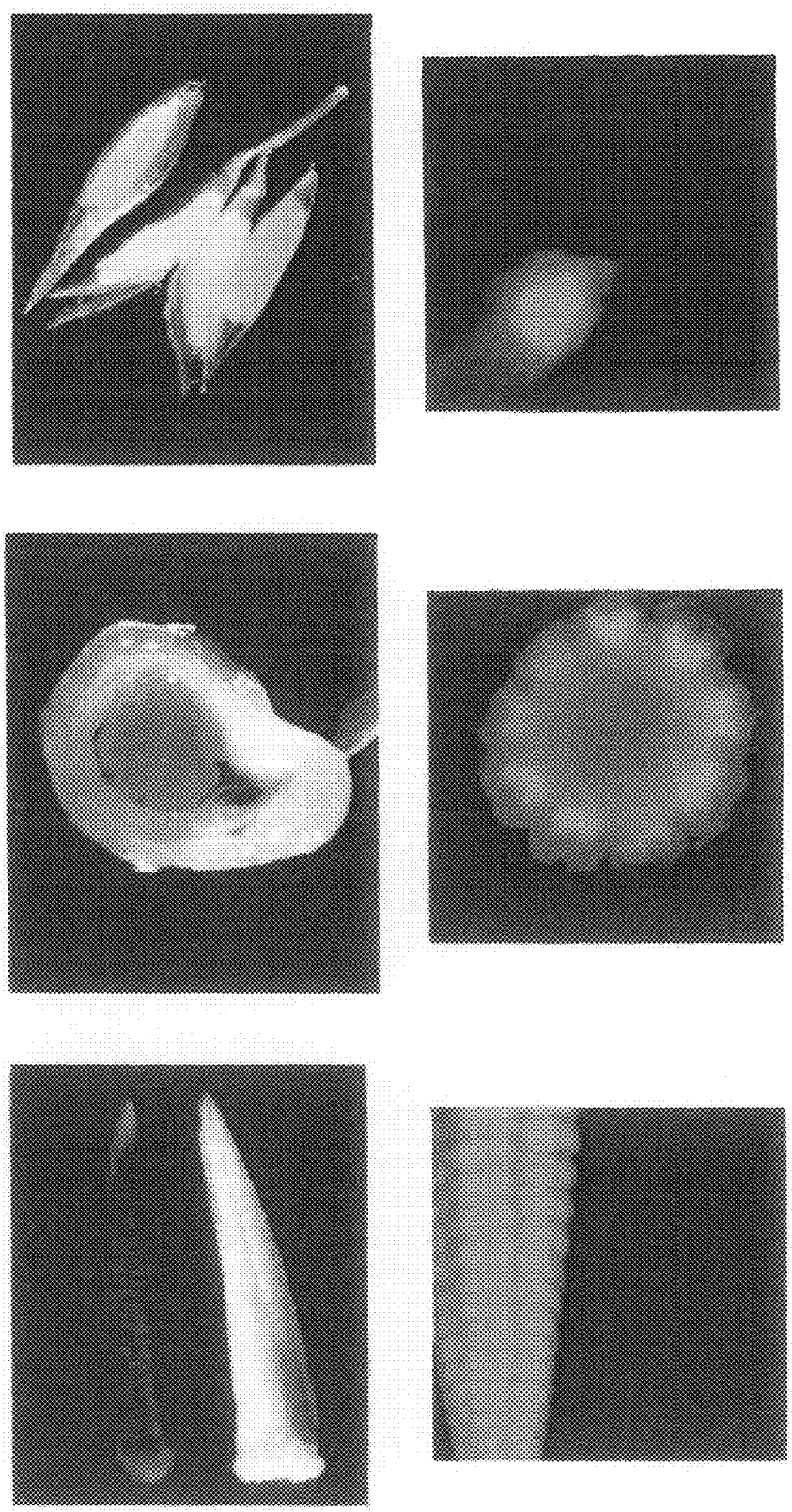
Figure 4B:
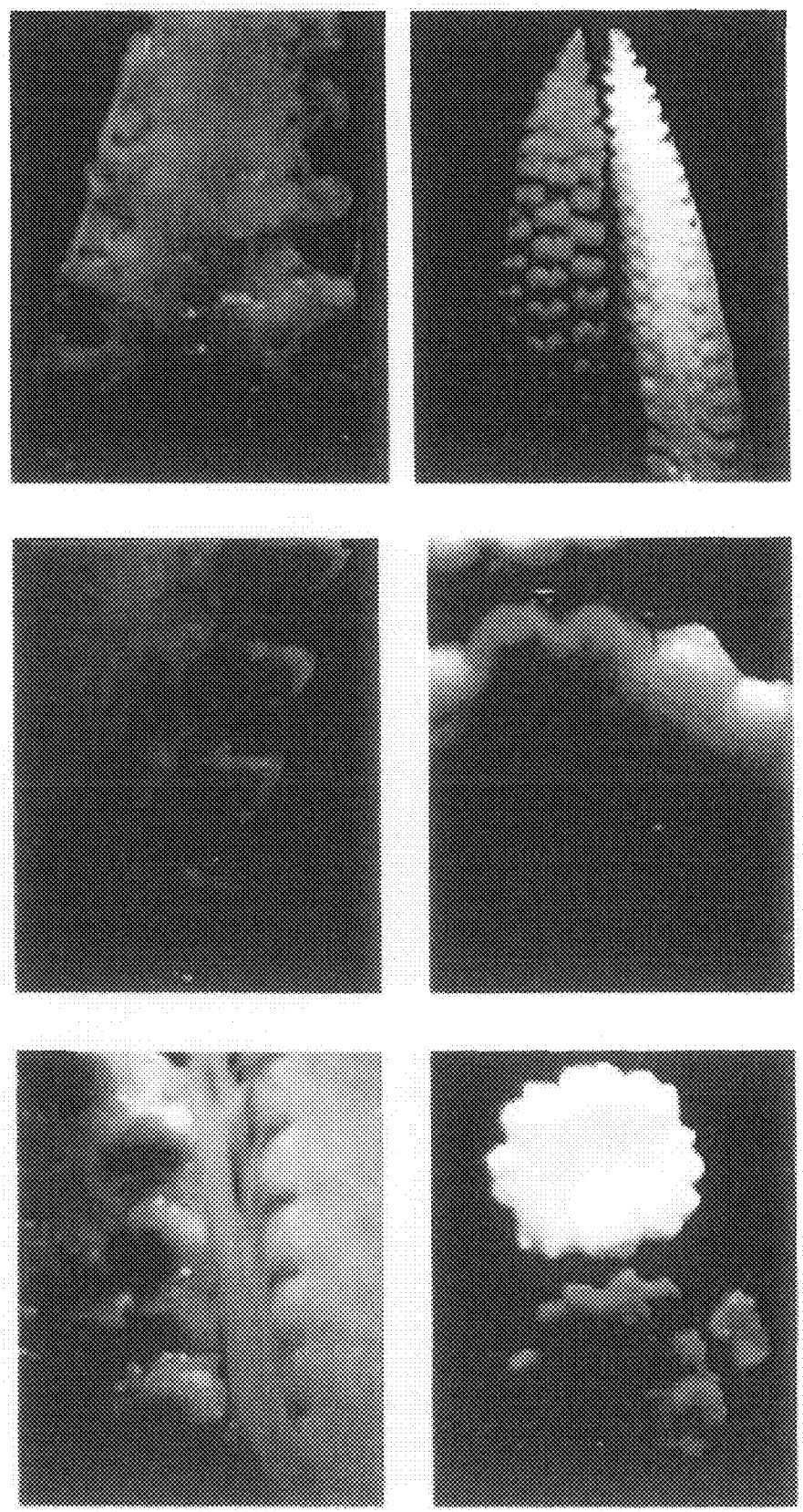
Figure 4F:
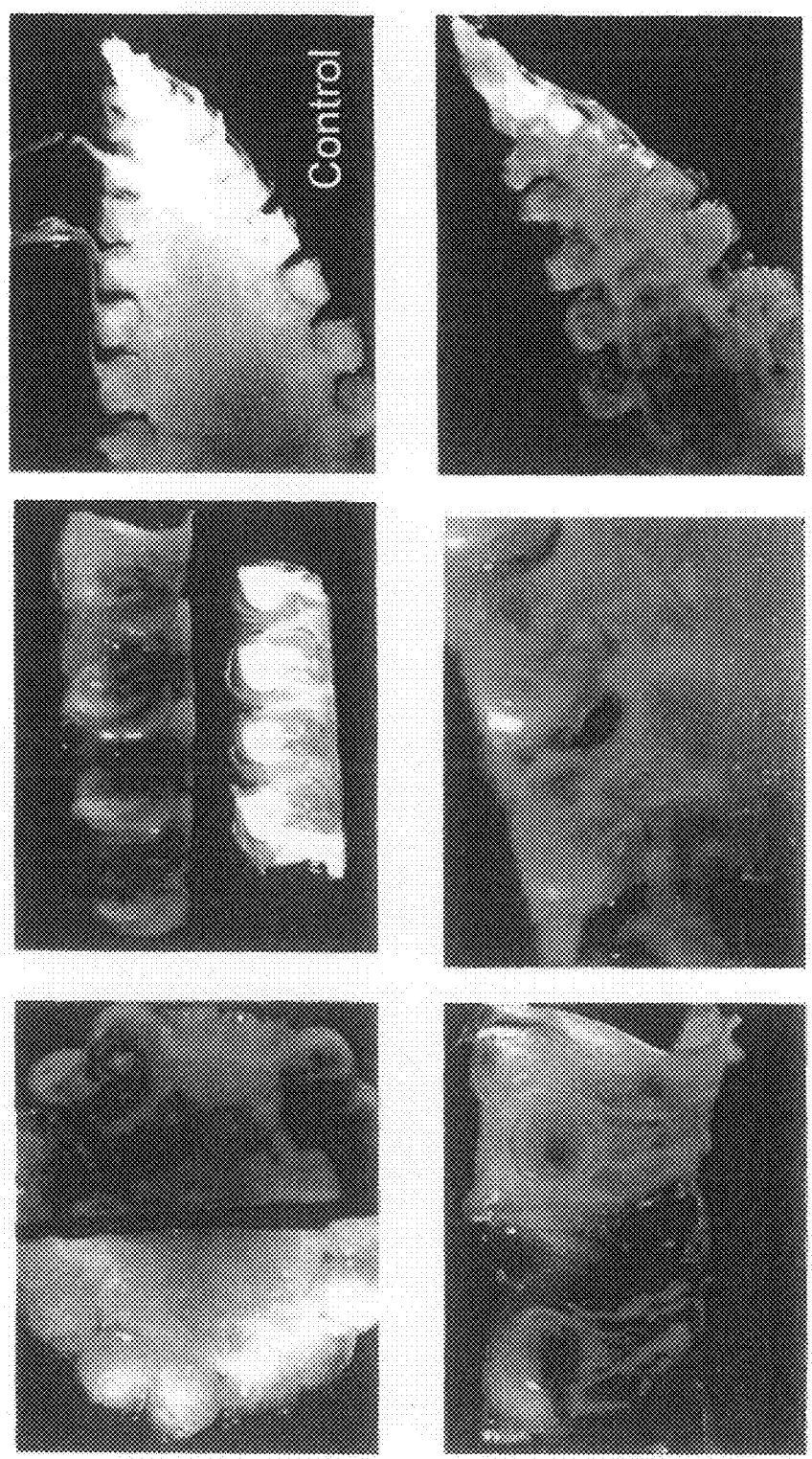
Figure 4G:
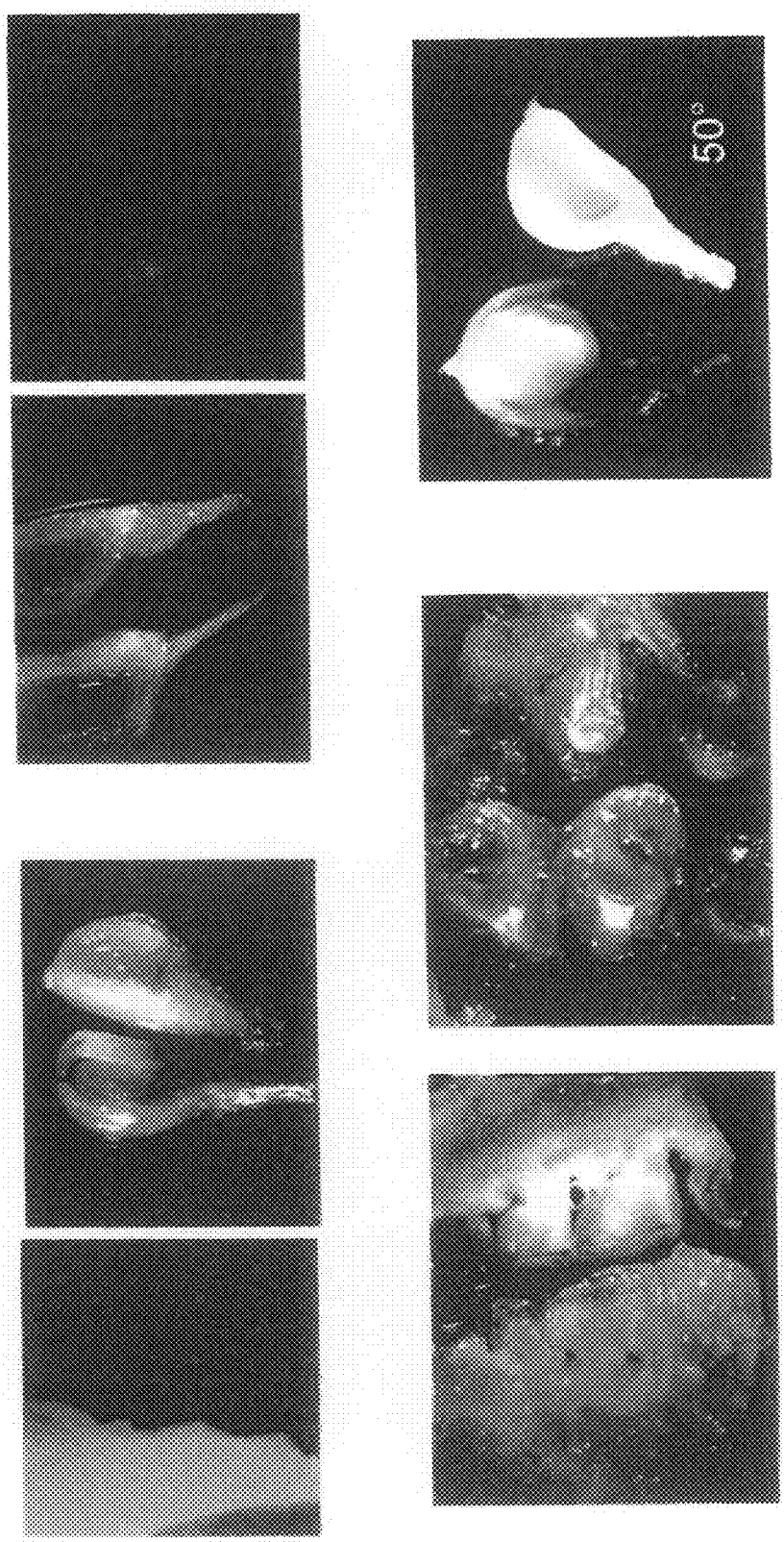
Figure 4H:
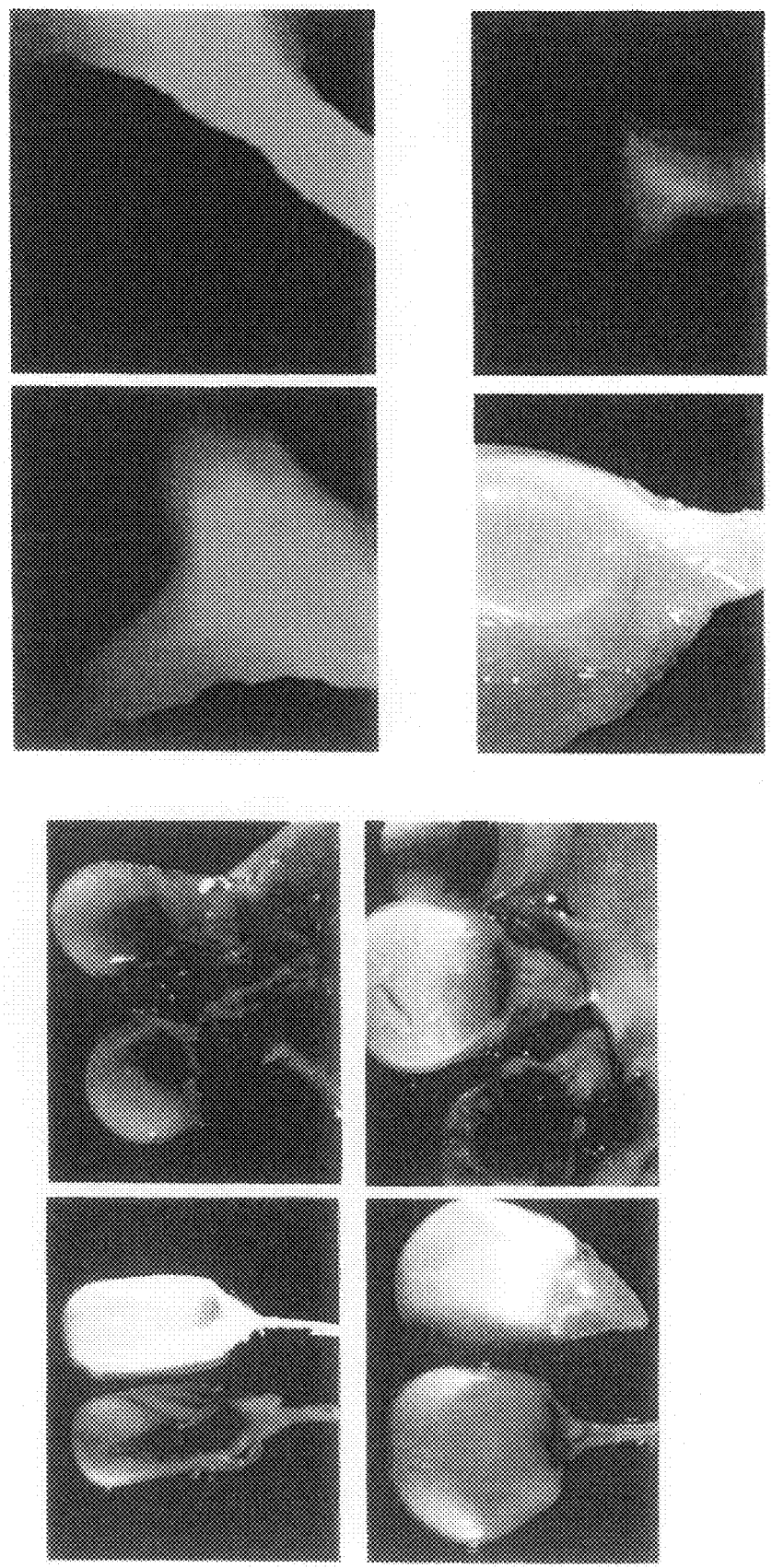

Where color photographs are provided, GUS expression appears blue and DS-RED is red. Where black-and-white photographs are provided, tissue expressing GUS is darker than control or non-expressing tissue.

DETAILED DESCRIPTION

The invention relates to compositions and methods drawn to plant promoters and methods of their use. The compositions comprise nucleotide sequences for a reproductive-tissue-preferred and preferentially an immature-ear-preferred promoter region for an actin depolymerization factor (ADF) gene, more particularly, the ADF4 promoter. The compositions further comprise DNA constructs comprising a nucleotide sequence for the promoter region of the actin depolymerization factor 4 (ADF4) gene operably linked to a heterologous nucleotide sequence of interest. In particular, the present invention provides for isolated nucleic acid molecules comprising the nucleotide sequence set forth in SEQ ID NO: 1, and fragments, variants, and complements thereof.

The ADF4 promoter sequences of the present invention include nucleotide constructs that allow initiation of transcription in a plant. In specific embodiments, the ADF4 promoter sequence allows initiation of transcription in a tissue-preferred, more particularly in an ear-preferred manner. Such constructs of the invention comprise regulated transcription initiation regions associated with plant developmental regulation. Thus, the compositions of the present invention include DNA constructs comprising a nucleotide sequence of interest operably linked to a plant promoter, particularly a reproductive-tissue-preferred promoter sequence for the ADF4 gene, more particularly a maize ADF4 promoter sequence. A sequence comprising the maize ADF promoter region is set forth in SEQ ID NO: 1.

Features of SEQ ID NO: 1 include the following: the ZmADF4 upstream regulatory region is shown from positions 7 to 1026. The untranslated leader of ZmADF4 appears at positions 1027 to 1147. The first intron of ZmADF4 is shown at positions 1151 to 1319. The first ATG is immediately before the 5' splice site. An intron may enhance expression; see, for example, Mun, et al., (2002) *Gene* 292(1-2): 233-243. A portion of the ZmADF4 coding sequence is shown from positions 1338 to 1385. This feature may facilitate the making of translational fusions with the promoter.

Compositions of the invention include the nucleotide sequences for the native ADF4 promoter and fragments and variants thereof. The promoter sequences of the invention are useful for expressing sequences. In specific embodiments, the promoter sequences of the invention are useful for expressing sequences of interest in a reproductive-tissue-preferred, particularly an ear-preferred manner. The nucleotide sequences of the invention also find use in the construction of expression vectors for subsequent expression of a heterologous nucleotide sequence in a plant of interest or as probes for the isolation of other ADF4-like promoters. In particular, the present invention provides for isolated DNA constructs comprising the ADF4 promoter nucleotide sequence set forth in SEQ ID NO: 1 operably linked to a nucleotide sequence of interest.

The invention encompasses isolated or substantially purified nucleic acid compositions. An "isolated" or "purified" nucleic acid molecule or biologically active portion thereof is substantially free of other cellular material, or culture medium when produced by recombinant techniques, or substantially free of chemical precursors or other chemicals when chemically synthesized. An "isolated" nucleic acid is substantially free of sequences (including protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. The ADF4 promoter sequences of the invention may be isolated from the 5' untranslated region flanking their respective transcription initiation sites.

Fragments and variants of the disclosed promoter nucleotide sequences are also encompassed by the present invention. In particular, fragments and variants of the ADF4 promoter sequence of SEQ ID NO: 1 may be used in the DNA constructs of the invention. As used herein, the term "fragment" refers to a portion of the nucleic acid sequence. Fragments of an ADF4 promoter sequence may retain the biological activity of initiating transcription, more particularly driving transcription in a reproductive tissue-preferred manner. Alternatively, fragments of a nucleotide sequence that are useful as hybridization probes may not necessarily retain biological activity. Fragments of a nucleotide sequence for the promoter region of the ADF4 gene may range from at least about 20 nucleotides, about 50 nucleotides, about 100 nucleotides, and up to the full-length nucleotide sequence of the invention for the promoter region of the gene.

A biologically active portion of an ADF4 promoter can be prepared by isolating a portion of the ADF4 promoter sequence of the invention, and assessing the promoter activity of the portion. Nucleic acid molecules that are fragments of an ADF4 promoter nucleotide sequence comprise at least about 16, 50, 75, 100, 150, 200, 250, 300, 350, 400, 450, 500, 550, 600, 650, 700, 800, 900, 1000, 1100, 1200, 1300 nucleotides, or up to the number of nucleotides present in a full-length ADF4 promoter sequence disclosed herein.

As used herein, the term "variants" is intended to mean sequences having substantial similarity with a promoter sequence disclosed herein. A variant comprises a deletion and/or addition of one or more nucleotides at one or more internal sites within the native polynucleotide and/or a substitution of one or more nucleotides at one or more sites in the native polynucleotide. As used herein, a "native" nucleotide sequence comprises a naturally occurring nucleotide sequence. For nucleotide sequences, naturally occurring variants can be identified with the use of well-known molecular biology techniques, such as, for example, with polymerase chain reaction (PCR) and hybridization techniques as outlined herein.

Variant nucleotide sequences also include synthetically derived nucleotide sequences, such as those generated, for example, by using site-directed mutagenesis. Generally, variants of a particular nucleotide sequence of the embodiments will have at least 40%, 50%, 60%, 65%, 70%, 75%, 80%, 85%, 90%, 91%, 92%, 93%, 94%, to 95%, 96%, 97%, 98%, 99% or more sequence identity to that particular nucleotide sequence as determined by sequence alignment programs described elsewhere herein using default parameters. Biologically active variants are also encompassed by the embodiments. Biologically active variants include, for example, the native promoter sequences of the embodiments having one or more nucleotide substitutions, deletions, or insertions. Promoter activity may be measured by using techniques such as Northern blot analysis, reporter activity measurements taken from transcriptional fusions, and the like. See, for example, Sambrook, et al., (1989) Molecular Cloning: A Laboratory Manual (2d ed., Cold Spring Harbor Laboratory Press, Cold Spring Harbor, N.Y.), hereinafter "Sambrook," herein incorporated by reference in its entirety. Alternatively, levels of a reporter gene such as green fluorescent protein (GFP) or the like produced under the control of a promoter fragment or variant can be measured. See, for example, U.S. Pat. No. 6,072,050, herein incorporated by reference in its entirety.

Variant nucleotide sequences also encompass sequences derived from a mutagenic and recombinogenic procedure such as DNA shuffling. With such a procedure, one or more different ADF4 nucleotide sequences for the promoter can be manipulated to create a new ADF4 promoter. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389 391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291; and U.S. Pat. Nos. 5,605,793 and 5,837,458, herein incorporated by reference in their entirety.

Methods for mutagenesis and nucleotide sequence alterations are well known in the art. See, for example, Kunkel (1985) *Proc. Natl. Acad. Sci. USA* 82:488-492; Kunkel, et al., (1987) *Methods in Enzymol.* 154:367-382; U.S. Pat. No. 4,873,192; Walker and Gaastra, eds. (1983) Techniques in Molecular Biology (MacMillan Publishing Company, New York) and the references cited therein, herein incorporated by reference in their entirety.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire ADF4 sequences set forth herein or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in, Sambrook, supra. See also, Innis, et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York), herein incorporated by reference in their entirety. Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$ or any other detectable marker. Thus, for example, probes for hybridization can be made by labeling synthetic oligonucleotides based on the ADF4 promoter sequences of the invention. Methods for preparation of probes for hybridization and for construction of genomic libraries are generally known in the art and are disclosed in Sambrook, supra.

For example, the entire ADF4 promoter sequence disclosed herein, or one or more portions thereof, may be used as a probe capable of specifically hybridizing to corresponding ADF4 promoter sequences and messenger RNAs. To achieve specific hybridization under a variety of conditions, such probes include sequences that are unique among ADF4 promoter sequences and are generally at least about 10 nucleotides in length or at least about 20 nucleotides in length. Such probes may be used to amplify corresponding ADF4 promoter sequences from a chosen plant by PCR. This technique may be used to isolate additional coding sequences from a desired organism, or as a diagnostic assay to determine the presence of coding sequences in an organism. Hybridization techniques include hybridization screening of plated DNA libraries (either plaques or colonies, see, for example, Sambrook, supra).

Hybridization of such sequences may be carried out under stringent conditions. The terms "stringent conditions" or "stringent hybridization conditions" are intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1 times to 2 times SSC (20 times SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5 times to 1 times SSC at 55 to 60° C. Exemplary high stringency conditions include hybridization in 50% formamide, 1 M NaCl, 1% SDS at 37° C., and a final wash in 0.1 times SSC at 60 to 65° C. for a duration of at least 30 minutes. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl, (1984) *Anal. Biochem* 138: 267 284: $T_m = 81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching, thus, $T_m$, hybridization, and/or wash conditions can be adjusted to hybridize to sequences of the desired identity. For example, if sequences with 90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3 or 4° C. lower than the $T_m$; moderately stringent conditions can utilize a hybridization and/or wash at 6, 7, 8, 9 or 10° C. lower than the $T_m$; low stringency conditions can utilize a hybridization and/or wash at 11, 12, 13, 14, 15 or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology—Hybridization with Nucleic Acid Probes, Part I, Chapter 2 (Elsevier, N.Y.); and Ausubel, et al., eds. (1995) Current Protocols in Molecular Biology, Chapter 2 (Greene Publishing and Wiley-Interscience, New York), herein incorporated by reference in their entirety. See also, Sambrook.

Thus, isolated sequences that have reproductive-tissue-preferred promoter activity, particularly immature-ear preferred promoter activity, and which hybridize under stringent conditions to the ADF4 promoter sequences disclosed herein, or to fragments thereof, are encompassed by the present invention.

In general, sequences that have promoter activity and hybridize to the promoter sequences disclosed herein will be at least 40% to 50% homologous, about 60%, 70%, 80%, 85%, 90%, 95% to 98% homologous or more with the disclosed sequences. That is, the sequence similarity of sequences may range, sharing at least about 40% to 50%, about 60% to 70%, and about 80%, 85%, 90%, 95% to 98% sequence similarity.

The following terms are used to describe the sequence relationships between two or more nucleic acids or polynucleotides: (a) "reference sequence", (b) "comparison window", (c) "sequence identity", (d) "percentage of sequence identity" and (e) "substantial identity".

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller, (1988) *CABIOS* 4:11-17; the algorithm of Smith, et al., (1981) *Adv. Appl. Math.* 2:482; the algorithm of Needleman and Wunsch, (1970) *J. Mol. Biol.* 48:443-453; the algorithm of Pearson and Lipman, (1988) *Proc. Natl. Acad. Sci.* 85:2444-2448; the algorithm of Karlin and Altschul, (1990) *Proc. Natl. Acad. Sci. USA* 872:264, modified as in Karlin and Altschul, (1993) *Proc. Natl. Acad. Sci. USA* 90:5873-5877, herein incorporated by reference in their entirety.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins, et al., (1988) *Gene* 73:237-244 (1988); Higgins, et al., (1989) *CABIOS* 5:151-153; Corpet, et al., (1988) *Nucleic Acids Res.* 16:10881-90; Huang, et al., (1992) *CABIOS* 8:155-65; and Pearson, et al., (1994) *Meth. Mol. Biol.* 24:307-331, herein incorporated by reference in their entirety. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul, et al., (1990) *J. Mol. Biol.* 215:403, herein incorporated by reference in its entirety, are based on the algorithm of Karlin and Altschul, (1990) supra. BLAST nucleotide searches can be performed with the BLASTN program, score=100, word length=12, to obtain nucleotide sequences homologous to a nucleotide sequence encoding a protein of the invention. BLAST protein searches can be performed with the BLASTX program, score=50, word length=3, to obtain amino acid sequences homologous to a protein or polypeptide of the invention. To obtain gapped alignments for comparison purposes, Gapped BLAST (in BLAST 2.0) can be utilized as described in Altschul, et al., (1997) *Nucleic Acids Res.* 25:3389, herein incorporated by reference in its entirety. Alternatively, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. See, the web site for the National Center for Biotechnology Information on the World Wide Web at ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. As used herein, "equivalent program" is any sequence comparison program that, for any two sequences in question, generates an alignment having identical nucleotide or amino acid residue matches and an identical percent sequence identity when compared to the corresponding alignment generated by GAP Version 10.

The GAP program uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see, Henikoff and Henikoff (1989) *Proc. Natl. Acad. Sci. USA* 89:10915, herein incorporated by reference in its entirety).

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of one and a non-conservative substitution is given a score of zero, a conservative substitution is given a score between zero and one. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, optimally at least 80%, more optimally at least 90%, and most optimally at least 95%, compared to a reference sequence using an alignment program using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, 70%, 80%, 90%, and at least 95%.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The ADF4 promoter sequence disclosed herein, as well as variants and fragments thereof, are useful for genetic engineering of plants, e.g. for the production of a transformed or transgenic plant, to express a phenotype of interest. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant DNA construct. It is to be understood that as used herein the term "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic.

A transgenic "event" is produced by transformation of plant cells with a heterologous DNA construct, including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual cross between the transformant and another plant wherein the progeny include the heterologous DNA.

As used herein, the term plant includes whole plants, plant organs (e.g., leaves, stems, roots, etc.), plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species include corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Heterologous coding sequences expressed by the ADF4 promoters of the invention may be used for varying the phenotype of a plant. Various changes in phenotype are of interest including modifying expression of a gene in a plant, altering a plant's pathogen or insect defense mechanism, increasing a plant's tolerance to herbicides, altering plant development to respond to environmental stress, modulating the plant's response to salt, temperature (hot and cold), drought, and the like. These results can be achieved by the expression of a heterologous nucleotide sequence of interest comprising an appropriate gene product. In specific embodiments, the heterologous nucleotide sequence of interest is an endogenous plant sequence whose expression level is increased in the plant or plant part. Results can be achieved by providing for altered expression of one or more endogenous gene products, particularly hormones, receptors, signaling molecules, enzymes, transporters, or cofactors, or by affecting nutrient uptake in the plant. Tissue-preferred expression as provided by the ADF promoter can target the alteration in expression to plant parts and/or growth stages of particular interest, such as developing reproductive tissues. These changes result in a change in phenotype of the transformed plant.

General categories of nucleotide sequences of interest for the present invention include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, environmental stress resistance (altered tolerance to cold, salt, drought, etc), and grain characteristics. Still other categories of transgenes include genes for inducing expression of exogenous products such as enzymes, cofactors, and hormones from plants and other eukaryotes as well as prokaryotic organisms. It is recognized that any gene of interest can be operably linked to the promoter of the invention and expressed in the plant.

Agronomically important traits that affect quality of grain, such as levels and types of oils, saturated and unsaturated, quality and quantity of essential amino acids, levels of cellulose, starch, and protein content can be genetically altered using the methods of the embodiments. Modifications to grain traits include, but are not limited to, increasing content of oleic acid, saturated and unsaturated oils, increasing levels of lysine and sulfur, providing essential amino acids, and modifying starch. Hordothionin protein modifications in corn are described in U.S. Pat. Nos. 5,990,389; 5,885,801; 5,885,802 and 5,703,049; herein incorporated by reference in their entirety. Another example is lysine and/or sulfur rich seed protein encoded by the soybean 2S albumin described in U.S. Pat. No. 5,850,016, filed Mar. 20, 1996, and the chymotrypsin inhibitor from barley, Williamson, et al., (1987) *Eur. J. Biochem* 165:99-106, the disclosures of which are herein incorporated by reference in their entirety.

Insect resistance genes may encode resistance to pests that have great yield drag such as rootworm, cutworm, European corn borer, and the like. Such genes include, for example, *Bacillus thuringiensis* toxic protein genes, U.S. Pat. Nos. 5,366,892; 5,747,450; 5,736,514; 5,723,756; 5,593,881; and Geiser, et al., (1986) *Gene* 48:109, the disclosures of which are herein incorporated by reference in their entirety. Genes encoding disease resistance traits include, for example, detoxification genes, such as those which detoxify fumonisin (U.S. Pat. No. 5,792,931); avirulence (avr) and disease resistance (R) genes (Jones, et al., (1994) *Science* 266:789; Martin, et al., (1993) *Science* 262:1432; and Mindrinos, et al., (1994) *Cell* 78:1089), herein incorporated by reference in their entirety.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), genes coding for resistance to glyphosate (e.g., the EPSPS gene and the GAT gene; see, for example, US Patent Application Publication Number 2004/0082770 and WO 03/092360, herein incorporated by reference in their entirety) or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Glyphosate resistance is imparted by mutant 5-enolpyruvl-3-phosphikimate synthase (EPSP) and aroA genes. See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications WO 97/04103; WO 97/04114; WO 00/66746; WO 01/66704; WO 00/66747 and WO 00/66748, which are incorporated herein by reference in their entirety. Glyphosate resistance is also imparted to plants that express a gene that encodes a glyphosate oxido-reductase enzyme as described more fully in U.S. Pat. Nos. 5,776,760 and 5,463,175, which are incorporated herein by reference in their entirety. In addition glyphosate resistance can be imparted to plants by the over expression of genes encoding glyphosate N-acetyltransferase. See, for example, U.S. patent application Ser. Nos. 11/405,845 and 10/427,692, herein incorporated by reference in their entirety.

Sterility genes can also be encoded in a DNA construct and provide an alternative to physical detasseling. Examples of genes used in such ways include male tissue-preferred genes and genes with male sterility phenotypes such as QM, described in U.S. Pat. No. 5,583,210, herein incorporated by reference in its entirety. Other genes include kinases and those encoding compounds toxic to either male or female gametophytic development.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321, herein incorporated by reference in its entirety. Genes such as .beta.-Ketothiolase, PHBase (polyhydroxybutyrate synthase), and acetoacetyl-CoA reductase (see, Schubert, et al., (1988) *J. Bacteriol.* 170:5837-5847, herein incorporated by reference in its entirety) facilitate expression of polyhydroxyalkanoates (PHAs).

Exogenous products include plant enzymes and products as well as those from other sources including prokaryotes and other eukaryotes. Such products include enzymes, cofactors, hormones, and the like.

Examples of other applicable genes and their associated phenotype include the gene which encodes viral coat protein and/or RNA, or other viral or plant genes that confer viral resistance; genes that confer fungal resistance; genes that promote yield improvement; and genes that provide for resistance to stress, such as cold, dehydration resulting from drought, heat and salinity, toxic metal or trace elements, or the like.

By way of illustration, without intending to be limiting, are examples of the types of genes which can be used in connection with the regulatory sequences of the invention.

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones, et al., (1994) *Science* 266:789 (cloning of the tomato Cf-9 gene for resistance to *Cladosporium fulvum*); Martin, et al., (1993) *Science* 262:1432 (tomato Pto gene for resistance to *Pseudomonas syringae* pv. tomato encodes a protein kinase); Mindrinos, et al., (1994) *Cell* 78:1089 (*Arabidopsis* RSP2 gene for resistance to *Pseudomonas syringae*); McDowell and Woffenden, (2003) *Trends Biotechnol.* 21(4):178-83 and Toyoda, et al., (2002) *Transgenic Res.* 11(6):567-82, herein incorporated by reference in their entirety. A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Numbers 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; WO 91/14778; WO 99/31248; WO 01/12731; WO 99/24581; WO 97/40162 and U.S. application Ser. Nos. 10/032,717; 10/414,637 and 10/606,320, herein incorporated by reference in their entirety.

(C) An insect-specific hormone or pheromone such as an ecdysteroid and juvenile hormone, a variant thereof, a mimetic based thereon, or an antagonist or agonist thereof. See, for example, the disclosure by Hammock, et al., (1990) *Nature* 344:458, of baculovirus expression of cloned juvenile hormone esterase, an inactivator of juvenile hormone, herein incorporated by reference in its entirety.

(D) An insect-specific peptide which, upon expression, disrupts the physiology of the affected pest. For example, see the disclosures of Regan, (1994) *J. Biol. Chem.* 269:9 (expression cloning yields DNA coding for insect diuretic hormone receptor); Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54; Zjawiony (2004) *J Nat Prod* 67(2):300-310; Carlini and Grossi-de-Sa (2002) *Toxicon* 40(11):1515-1539; Ussuf, et al., (2001) *Curr Sci.* 80(7):847-853; and Vasconcelos and Oliveira (2004) *Toxicon* 44(4):385-403, herein incorporated by reference in their entirety. See also, U.S. Pat. No. 5,266,317 to Tomalski, et al., who disclose genes encoding insect-specific toxins, herein incorporated by reference in its entirety.

(E) An enzyme responsible for a hyperaccumulation of a monterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application Number WO 93/02197 in the name of Scott, et al., which discloses the nucleotide sequence of a callase gene, herein incorporated by reference in its entirety. DNA molecules which contain chitinase-encoding sequences can be obtained, for example, from the ATCC under Accession Numbers 39637 and 67152. See also, Kramer, et al., (1993) *Insect Biochem. Molec. Biol.* 23:691, who teach the nucleotide sequence of a cDNA encoding tobacco hookworm chitinase, and Kawalleck, et al., (1993) *Plant Molec. Biol.* 21:673, who provide the nucleotide sequence of the parsley ubi4-2 polyubiquitin gene, U.S. patent application Ser. Nos. 10/389,432, 10/692,367 and U.S. Pat. No. 6,563,020, herein incorporated by reference in their entirety.

(G) A molecule that stimulates signal transduction. For example, see the disclosure by Botella, et al., (1994) *Plant Molec. Biol.* 24:757, of nucleotide sequences for mung bean calmodulin cDNA clones, and Griess, et al., (1994) *Plant Physiol.* 104:1467, who provide the nucleotide sequence of a maize calmodulin cDNA clone, herein incorporated by reference in their entirety.

(H) A hydrophobic moment peptide. See, PCT Application Number WO 95/16776 and U.S. Pat. No. 5,580,852 (disclosure of peptide derivatives of Tachyplesin which inhibit fungal plant pathogens) and PCT Application Number WO 95/18855 and U.S. Pat. No. 5,607,914) (teaches synthetic antimicrobial peptides that confer disease resistance), herein incorporated by reference in their entirety.

(I) A membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum*, herein incorporated by reference in its entirety.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451, herein incorporated by reference in its entirety. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments), herein incorporated by reference in its entirety.

(L) A virus-specific antibody. See, for example, Tavladoraki, et al., (1993) *Nature* 366:469, who show that transgenic plants expressing recombinant antibody genes are protected from virus attack, herein incorporated by reference in its entirety.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436, herein incorporated by reference in its entirety. The cloning and characterization of a gene which encodes a bean endopolygalacturonase-inhibiting protein is described by Toubart, et al., (1992) *Plant J.* 2:367, herein incorporated by reference in its entirety.

(N) A developmental-arrestive protein produced in nature by a plant. For example, Logemann, et al., (1992) *Bio/Technology* 10:305, herein incorporated by reference in its entirety, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) *Current Biology* 5(2):128-131, Pieterse and Van Loon (2004) *Curr. Opin. Plant Bio.* 7(4):456-64 and Somssich (2003) *Cell* 113(7):815-6, herein incorporated by reference in their entirety.

(P) Antifungal genes (Cornelissen and Melchers, (1993) *Pl. Physiol.* 101:709-712, and Parijs, et al., (1991) *Planta* 183:258-264 and Bushnell, et al., (1998) *Can. J. of Plant Path.* 20(2):137-149. Also see, U.S. patent application Ser. No. 09/950,933, herein incorporated by reference in their entirety.

(Q) Detoxification genes, such as for fumonisin, beauvericin, moniliformin and zearalenone and their structurally related derivatives. For example, see U.S. Pat. No. 5,792,931, herein incorporated by reference in its entirety.

(R) Cystatin and cysteine proteinase inhibitors. See, U.S. application Ser. No. 10/947,979, herein incorporated by reference in its entirety.

(S) Defensin genes. See, WO03000863 and U.S. application Ser. No. 10/178,213, herein incorporated by reference in their entirety.

(T) Genes conferring resistance to nematodes. See, WO 03/033651 and Urwin, et. al., (1998) *Planta* 204:472-479, Williamson (1999) *Curr Opin Plant Bio.* 2(4):327-31, herein incorporated by reference in their entirety.

(U) Genes such as rcg1 conferring resistance to Anthracnose stalk rot, which is caused by the fungus *Colletotrichum graminiola*. See, Jung, et al., Generation-means analysis and quantitative trait locus mapping of Anthracnose Stalk Rot genes in Maize, *Theor. Appl. Genet.* (1994) 89:413-418 as well as U.S. Patent Application No. 60/675,664, herein incorporated by reference in their entirety.

2. Transgenes that Confer Resistance to a Herbicide, for Example:

(A) A herbicide that inhibits the growing point or meristem, such as an imidazolinone or a sulfonylurea. Exemplary genes in this category code for mutant ALS and AHAS enzyme as described, for example, by Lee, et al., (1988) *EMBO J.* 7:1241, and Miki, et al., (1990) *Theor. Appl. Genet.* 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824; and international publication WO 96/33270, which are incorporated herein by reference in their entirety.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E and 5,491,288; and international publications EP1173580; WO 01/66704; EP1173581 and EP1173582, which are incorporated herein by reference in their entirety. Glyphosate resistance is also imparted to plants that express a gene that encodes a glyphosate oxido-reductase enzyme as described more fully in U.S. Pat. Nos. 5,776,760 and 5,463,175, which are incorporated herein by reference in their entirety. In addition glyphosate resistance can be imparted to plants by the over expression of genes encoding glyphosate N-acetyltransferase. See, for example, U.S. patent application Ser. Nos. 11/405,845 and 10/427,692, and PCT Application Number US01/46227, herein incorporated by reference in their entirety. A DNA molecule encoding a mutant aroA gene can be obtained under ATCC accession No. 39256, and the nucleotide sequence of the mutant gene is disclosed in U.S. Pat. No. 4,769,061 to Comai, herein incorporated by reference in its entirety. European Patent Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin, herein incorporated by reference in their entirety. The nucleotide sequence of a phosphinothricin-acetyl-transferase gene is provided in European Patent Numbers 0 242 246 and 0 242 236 to Leemans, et al., De Greef, et al., (1989) *Bio/Technology* 7:61 which describe the production of transgenic plants that express chimeric bar genes coding for phosphinothricin acetyl transferase activity, herein incorporated by reference in their entirety. See also, U.S. Pat. Nos. 5,969,213; 5,489,520; 5,550,318; 5,874,265; 5,919,675; 5,561,236; 5,648,477; 5,646,024; 6,177,616 B1 and 5,879,903, herein incorporated by reference in their entirety. Exemplary genes conferring resistance to phenoxy proprionic acids and cycloshexones, such as sethoxydim and haloxyfop, are the Acc1-S1, Acc1-S2 and Acc1-S3 genes described by Marshall, et al., (1992) *Theor. Appl. Genet.* 83:435, herein incorporated by reference in its entirety.

(C) A herbicide that inhibits photosynthesis, such as a triazine (psbA and gs+ genes) and a benzonitrile (nitrilase gene). Przibilla, et al., (1991) *Plant Cell* 3:169, herein incorporated by reference in its entirety, describe the transformation of *Chlamydomonas* with plasmids encoding mutant psbA genes. Nucleotide sequences for nitrilase genes are disclosed in U.S. Pat. No. 4,810,648 to Stalker, herein incorporated by reference in its entirety, and DNA molecules containing these genes are available under ATCC Accession Numbers 53435, 67441 and 67442. Cloning and expression of DNA coding for a glutathione S-transferase is described by Hayes, et al., (1992) *Biochem. J.* 285:173, herein incorporated by reference in its entirety.

(D) Acetohydroxy acid synthase, which has been found to make plants that express this enzyme resistant to multiple types of herbicides, has been introduced into a variety of plants (see, e.g., Hattori, et al., (1995) *Mol Gen Genet* 246: 419, herein incorporated by reference in its entirety). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol.* 106(1):17-23), genes for glutathione reductase and superoxide dismutase (Aono, et al., (1995) *Plant Cell Physiol* 36:1687, and genes for various phosphotransferases (Datta, et al., (1992) *Plant Mol Biol* 20:619), herein incorporated by reference in their entirety.

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1 and 5,767,373; and international publication number WO 01/12825, herein incorporated by reference in their entirety.

3. Transgenes that Confer or Contribute to an Altered Grain Characteristic, Such as:

(A) Altered fatty acids, for example, by
(1) Down-regulation of stearoyl-ACP desaturase to increase stearic acid content of the plant. See, Knultzon, et al., (1992) *Proc. Natl. Acad. Sci. USA* 89:2624 and WO99/64579 (Genes for Desaturases to Alter Lipid Profiles in Corn), herein incorporated by reference in their entirety,
(2) Elevating oleic acid via FAD-2 gene modification and/ or decreasing linolenic acid via FAD-3 gene modification (see, U.S. Pat. Nos. 6,063,947; 6,323,392; 6,372,965 and WO 93/11245, herein incorporated by reference in their entirety),
(3) Altering conjugated linolenic or linoleic acid content, such as in WO 01/12800, herein incorporated by reference in its entirety,
(4) Altering LEC1, AGP, Dek1, Superal1, milps, various lpa genes such as lpa1, lpa3, hpt or hggt. For example, see, WO 02/42424, WO 98/22604, WO 03/011015, U.S. Pat. No. 6,423,886, U.S. Pat. No. 6,197,561, U.S. Pat. No. 6,825,397, US Patent Application Publication Numbers 2003/0079247, 2003/0204870, WO02/057439, WO03/011015 and Rivera-Madrid, et. al., (1995) *Proc. Natl. Acad. Sci.* 92:5620-5624, herein incorporated by reference in their entirety.

(B) Altered phosphorus content, for example, by the
(1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene, herein incorporated by reference in its entirety.
(2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy, et al., (1990) *Maydica* 35:383 and/or by altering inositol kinase activity as in WO 02/059324, US Patent Application Publication Number 2003/0009011, WO 03/027243, US Patent Application Publication Number 2003/0079247, WO 99/05298, U.S. Pat. No. 6,197,561, U.S. Pat. No. 6,291,224, U.S. Pat. No. 6,391,348, WO2002/059324, US Patent Application Publication Number 2003/0079247, WO98/45448, WO99/55882, WO01/04147, herein incorporated by reference in their entirety.

(C) Altered carbohydrates effected, for example, by altering a gene for an enzyme that affects the branching pattern of starch or a gene altering thioredoxin such as NTR and/or TRX (see, U.S. Pat. No. 6,531,648, which is incorporated by reference in its entirety) and/or a gamma zein knock out or mutant such as cs27 or TUSC27 or en27 (see, U.S. Pat. No. 6,858,778 and US Patent Application Publication Numbers 2005/0160488 and 2005/0204418; which are incorporated by reference in its entirety). See, Shiroza, et al., (1988) *J. Bacteriol.* 170:810 (nucleotide sequence of *Streptococcus mutans* fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec. Biol.* 21:515 (nucleotide sequences of tomato invertase genes), Søgaard, et al., (1993) *J. Biol. Chem.* 268:22480 (site-directed mutagenesis of barley alpha-amylase gene), and Fisher, et al., (1993) *Plant Physiol.* 102:1045 (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)), herein incorporated by reference in their entirety. The fatty acid modification genes mentioned above may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US Patent Application Publication Number 2004/0034886 and WO 00/68393 involving the manipulation of antioxidant levels through alteration of a phytl prenyl transferase (ppt), WO 03/082899 through alteration of a homogentisate geranyl geranyl transferase (hggt), herein incorporated by reference in their entirety.

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US Patent Application Publication Number 2003/0163838, US Patent Application Publication Number 2003/0150014, US Patent Application Publication Number 2004/0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US Patent Application Publication Number 2004/0025203 (UDPGdH), U.S. Pat. No. 6,194,638 (RGP), herein incorporated by reference in their entirety.

4. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511, herein incorporated by reference in their entirety. In addition to these methods, Albertsen, et al., U.S. Pat. No. 5,432,068, herein incorporated by reference in its entirety, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N-Ac-PPT (WO 01/29237, herein incorporated by reference in its entirety).

(B) Introduction of various stamen-specific promoters (WO 92/13956, WO 92/13957, herein incorporated by reference in their entirety).

(C) Introduction of the barnase and the barstar gene (Paul, et al., (1992) *Plant Mol. Biol.* 19:611-622, herein incorporated by reference in its entirety).

For additional examples of nuclear male and female sterility systems and genes, see also, U.S. Pat. Nos. 5,859,341; 6,297,426; 5,478,369; 5,824,524; 5,850,014 and 6,265,640; all of which are hereby incorporated by reference in their entirety.

5. Genes that create a site for site specific DNA integration. This includes the introduction of FRT sites that may be used in the FLP/FRT system and/or Lox sites that may be used in the Cre/Loxp system. For example, see Lyznik, et al., (2003) Site-Specific Recombination for Genetic Engineering in Plants, Plant Cell Rep 21:925-932 and WO 99/25821, which are hereby incorporated by reference in their entirety. Other systems that may be used include the Gin recombinase of phage Mu (Maeser, et al., 1991; Vicki Chandler, *The Maize Handbook* ch. 118 (Springer-Verlag 1994), the Pin recombinase of *E. coli* (Enomoto, et al., 1983), and the R/RS system of the pSR1 plasmid (Araki, et al., 1992), herein incorporated by reference in their entirety.

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see WO 00/73475 where water use efficiency is altered through alteration of malate; U.S. Pat. No. 5,892,009, U.S. Pat. No. 5,965,705, U.S. Pat. No. 5,929,305, U.S. Pat. No. 5,891,859, U.S. Pat. No. 6,417,428, U.S. Pat. No. 6,664,446, U.S. Pat. No. 6,706,866, U.S. Pat. No. 6,717,034, WO2000060089, WO2001026459, WO2001035725, WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521, and WO9938977 describing genes, including CBF genes and transcription factors effective in mitigating the negative effects of freezing, high salinity, and drought on plants, as well as conferring other positive effects on plant phenotype; US Patent Application Publication Number 2004/0148654 and WO01/36596 where abscisic acid is altered in plants resulting in improved plant phenotype such as increased yield and/or increased tolerance to abiotic stress; WO2000/006341, WO04/090143, U.S. patent application Ser. No. 10/817,483 and U.S. Pat. No. 6,992,237, where cytokinin expression is modified resulting in plants with increased stress tolerance, such as drought tolerance, and/or increased yield, herein incorporated by reference in their entirety. Also see WO0202776, WO2003052063, JP2002281975, U.S. Pat. No. 6,084,153, WO0164898, U.S. Pat. No. 6,177,275, and U.S. Pat. No. 6,107,547 (enhancement of nitrogen utilization and altered nitrogen responsiveness), herein incorporated by reference in their entirety. For ethylene alteration, see US Patent Application Publication Number 2004/0128719, US Patent Application Publication Number 2003/0166197 and WO200032761, herein incorporated by reference in their entirety. For plant transcription factors or transcriptional regulators of abiotic stress, see, e.g., US Patent Application Publication Number 2004/0098764 or US Patent Application Publication Number 2004/0078852, herein incorporated by reference in their entirety.

Other genes and transcription factors that affect plant growth and agronomic traits such as yield, flowering, plant growth and/or plant structure, can be introduced or introgressed into plants, see, e.g., WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. No. 6,794,560, U.S. Pat. No. 6,307,126 (GAI), WO99/09174 (D8 and Rht), and WO2004076638 and WO2004031349 (transcription factors), herein incorporated by reference in their entirety.

The heterologous nucleotide sequence operably linked to the ADF promoter and its related biologically active fragments or variants disclosed herein may be an antisense sequence for a targeted gene. The terminology "antisense DNA nucleotide sequence" is intended to mean a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Modifications of the antisense sequences may be made as long as the sequences hybridize to and interfere with expression of the corresponding mRNA. In this manner, antisense constructions having 70%, 80%, 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used. Thus, the promoter sequences disclosed herein may be operably linked to antisense DNA sequences to reduce or inhibit expression of a native protein in the plant.

"RNAi" refers to a series of related techniques to reduce the expression of genes (see, for example, U.S. Pat. No. 6,506,559, herein incorporated by reference in its entirety). Older techniques referred to by other names are now thought to rely on the same mechanism, but are given different names in the literature. These include "antisense inhibition," the production of antisense RNA transcripts capable of suppressing the expression of the target protein, and "co-suppression" or "sense-suppression," which refer to the production of sense RNA transcripts capable of suppressing the expression of identical or substantially similar foreign or endogenous genes (U.S. Pat. No. 5,231,020, incorporated herein by reference in its entirety). Such techniques rely on the use of constructs resulting in the accumulation of double stranded RNA with one strand complementary to the target gene to be silenced. The ADF4 promoters of the embodiments may be used to drive expression of constructs that will result in RNA interference including microRNAs and siRNAs.

As used herein, the terms "promoter" or "transcriptional initiation region" mean a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Additionally, chimeric promoters may be provided. Such chimeras include portions of the promoter sequence fused to fragments and/or variants of heterologous transcriptional regulatory regions. Thus, the promoter regions disclosed herein can comprise upstream regulatory elements such as, those responsible for tissue and temporal expression of the coding sequence, enhancers and the like. In the same manner, the promoter elements, which enable expression in the desired tissue such as reproductive tissue, can be identified, isolated and used with other core promoters to confer reproductive-tissue-preferred expression. In this aspect of the invention, "core promoter" is intended to mean a promoter without promoter elements.

As used herein, the term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements that modify gene expression. It is to be understood that nucleotide sequences, located within introns or 3' of the coding region sequence may also contribute to the regulation of expression of a coding region of interest. Examples of suitable introns include, but are not limited to, the maize IVS6 intron, or the maize actin intron. A regulatory element may also include those elements located downstream (3') to the site of transcription initiation, or within transcribed regions, or both. In the context of the present invention a post-transcriptional regulatory element may include elements that are active following transcription initiation, for example translational and transcriptional enhancers, translational and transcriptional repressors, and mRNA stability determinants.

The regulatory elements, or variants or fragments thereof, of the present invention may be operatively associated with heterologous regulatory elements or promoters in order to modulate the activity of the heterologous regulatory element. Such modulation includes enhancing or repressing transcriptional activity of the heterologous regulatory element, modulating post-transcriptional events, or either enhancing or repressing transcriptional activity of the heterologous regulatory element and modulating post-transcriptional events. For example, one or more regulatory elements, or fragments thereof, of the present invention may be operatively associated with constitutive, inducible, or tissue specific promoters or fragment thereof, to modulate the activity of such promoters within desired tissues in plant cells.

The regulatory sequences of the present invention, or variants or fragments thereof, when operably linked to a heterologous nucleotide sequence of interest can drive reproductive-tissue-preferred expression, preferentially ear-preferred expression, of the heterologous nucleotide sequence in the reproductive tissue of the plant expressing this construct. The term "reproductive-tissue-preferred," means that expression of the heterologous nucleotide sequence is most abundant in the reproductive tissue. While some level of expression of the heterologous nucleotide sequence may occur in other plant tissue types, expression occurs most abundantly in the reproductive tissue.

A "heterologous nucleotide sequence" is a sequence that is not naturally occurring with the promoter sequence of the invention. While this nucleotide sequence is heterologous to the promoter sequence, it may be homologous, or native, or heterologous, or foreign, to the plant host.

The isolated promoter sequences of the present invention can be modified to provide for a range of expression levels of the heterologous nucleotide sequence. Thus, less than the entire promoter region may be utilized and the ability to drive expression of the nucleotide sequence of interest retained. It is recognized that expression levels of the mRNA may be altered in different ways with deletions of portions of the promoter sequences. The mRNA expression levels may be decreased, or alternatively, expression may be increased as a result of promoter deletions if, for example, there is a negative regulatory element (for a repressor) that is removed during the truncation process. Generally, at least about 20 nucleotides of an isolated promoter sequence will be used to drive expression of a nucleotide sequence.

It is recognized that to increase transcription levels, enhancers may be utilized in combination with the promoter regions of the invention. Enhancers are nucleotide sequences that act to increase the expression of a promoter region. Enhancers are known in the art and include the SV40 enhancer region, the 35S enhancer element, and the like. Some enhancers are also known to alter normal promoter expression patterns, for example, by causing a promoter to be expressed constitutively when without the enhancer, the same promoter is expressed only in one specific tissue or a few specific tissues.

Modifications of the isolated promoter sequences of the present invention can provide for a range of expression of the heterologous nucleotide sequence. Thus, they may be modified to be weak promoters or strong promoters. Generally, a "weak promoter" means a promoter that drives expression of a coding sequence at a low level. A "low level" of expression is intended to mean expression at levels of about $1/10,000$ transcripts to about $1/100,000$ transcripts to about $1/500,000$ transcripts. Conversely, a strong promoter drives expression of a coding sequence at a high level, or at about $1/10$ transcripts to about $1/100$ transcripts to about $1/1,000$ transcripts.

It is recognized that the promoters of the invention may be used with their native ADF4 coding sequences to increase or decrease expression, thereby resulting in a change in phenotype of the transformed plant. The nucleotide sequences disclosed in the present invention, as well as variants and fragments thereof, are useful in the genetic manipulation of any plant. The ADF4 promoter sequences are useful in this aspect when operably linked with a heterologous nucleotide sequence whose expression is to be controlled to achieve a desired phenotypic response. The term "operably linked" means that the transcription or translation of the heterologous nucleotide sequence is under the influence of the promoter sequence. In this manner, the nucleotide sequences for the promoters of the invention may be provided in expression cassettes along with heterologous nucleotide sequences of interest for expression in the plant of interest, more particularly for expression in the reproductive tissue of the plant.

In one embodiment of the invention, expression cassettes will comprise a transcriptional initiation region comprising one of the promoter nucleotide sequences of the present invention, or variants or fragments thereof, operably linked to the heterologous nucleotide sequence. Such an expression cassette can be provided with a plurality of restriction sites for insertion of the nucleotide sequence to be under the transcriptional regulation of the regulatory regions. The expression cassette may additionally contain selectable marker genes as well as 3' termination regions.

The expression cassette can include, in the 5'-3' direction of transcription, a transcriptional initiation region (i.e., a promoter, or variant or fragment thereof, of the invention), a translational initiation region, a heterologous nucleotide sequence of interest, a translational termination region and, optionally, a transcriptional termination region functional in the host organism. The regulatory regions (i.e., promoters, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

While it may be preferable to express a heterologous nucleotide sequence using the promoters of the invention, the native sequences may be expressed. Such constructs would change expression levels of the ADF4 protein in the plant or plant cell. Thus, the phenotype of the plant or plant cell is altered.

The termination region may be native with the transcriptional initiation region, may be native with the operably linked DNA sequence of interest, may be native with the plant host, or may be derived from another source (i.e., foreign or heterologous to the promoter, the DNA sequence being expressed, the plant host, or any combination thereof). Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903; and Joshi, et al., (1987) *Nucleic Acid Res.* 15:9627-9639, herein incorporated by reference in their entirety.

The expression cassette comprising the sequences of the present invention may also contain at least one additional nucleotide sequence for a gene to be cotransformed into the organism. Alternatively, the additional sequence(s) can be provided on another expression cassette.

Where appropriate, the nucleotide sequences whose expression is to be under the control of the reproductive-tissue-preferred promoter sequence of the present invention and any additional nucleotide sequence(s) may be optimized for increased expression in the transformed plant. That is, these nucleotide sequences can be synthesized using plant preferred codons for improved expression. See, for example, Campbell and Gowri (1990) *Plant Physiol.* 92:1-11, herein incorporated by reference in its entirety, for a discussion of host-preferred codon usage. Methods are available in the art for synthesizing plant-preferred genes. See, for example, U.S. Pat. Nos. 5,380,831, 5,436,391 and Murray, et al., (1989) *Nucleic Acids Res.* 17:477-498, herein incorporated by reference in their entirety.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include, without limitation: picornavirus leaders, for example, EMCV leader (Encephalomyocarditis 5' noncoding region) (Elroy-Stein, et al., (1989) *Proc. Nat. Acad. Sci. USA* 86:6126-6130); potyvirus leaders, for example, TEV leader (Tobacco Etch Virus) (Allison, et al., (1986) *Virology* 154:9-20); MDMV leader (Maize Dwarf Mosaic Virus); human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) *Molecular Biology of RNA*, pages 237-256); and maize chlorotic mottle virus leader (MCMV) (Lommel, et al., (1991) *Virology* 81:382-385), herein incorporated by reference in their entirety. See, also, Della-Cioppa, et al., (1987) *Plant Physiology* 84:965-968, herein incorporated by reference in its entirety. Methods known to enhance mRNA stability can also be utilized, for example, introns, such as the maize Ubiquitin intron (Christensen and Quail (1996) *Transgenic Res.* 5:213-218; Christensen, et al., (1992) *Plant Molecular Biology* 18:675-689) or the maize AdhI intron (Kyozuka, et al., (1991) *Mol. Gen. Genet.* 228:40-48; Kyozuka, et al., (1990) *Maydica* 35:353-357), and the like, herein incorporated by reference in their entirety.

The DNA constructs of the embodiments can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA. It is recognized that to increase transcription levels enhancers may be utilized in combination with the promoter regions of the embodiments. Enhancers are known in the art and include the SV40 enhancer region, the 35S enhancer element, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

Reporter genes or selectable marker genes may also be included in the expression cassettes of the present invention. Examples of suitable reporter genes known in the art can be found in, for example, Jefferson, et al., (1991) in Plant Molecular Biology Manual, ed. Gelvin, et al., (Kluwer Academic Publishers), pp. 1-33; DeWet, et al., (1987) *Mol. Cell. Biol.* 7:725-737; Goff, et al., (1990) *EMBO J.* 9:2517-2522; Kain, et al., (1995) *Bio Techniques* 19:650-655 and Chiu, et al., (1996) *Current Biology* 6:325-330, herein incorporated by reference in their entirety.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213; Meijer, et al., (1991) *Plant Mol. Biol.* 16:807-820); hygromycin (Waldron, et al., (1985) *Plant Mol. Biol.* 5:103-108 and Zhijian, et al., (1995) *Plant Science* 108:219-227); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-36); bromoxynil (Stalker, et al., (1988) *Science* 242:419-423); glyphosate (Shaw, et al., (1986) *Science* 233:478-481; and U.S. patent application Ser. Nos. 10/004,357 and 10/427,692); phosphinothricin (DeBlock, et al., (1987) *EMBO J.* 6:2513-2518), herein incorporated by reference in their entirety.

Other genes that could serve utility in the recovery of transgenic events would include, but are not limited to, examples such as GUS (beta-glucuronidase; Jefferson (1987) *Plant Mol. Biol. Rep.* 5:387), GFP (green fluorescence protein; Chalfie, et al., (1994) *Science* 263:802), luciferase (Riggs, et al., (1987) *Nucleic Acids Res.* 15(19):8115 and Luehrsen, et al., (1992) *Methods Enzymol.* 216:397-414) and the maize genes encoding for anthocyanin production (Ludwig, et al., (1990) *Science* 247:449), herein incorporated by reference in their entirety.

The expression cassette comprising the ADF4 promoter of the present invention operably linked to a nucleotide sequence of interest can be used to transform any plant. In this manner, genetically modified plants, plant cells, plant tissue, seed, root, and the like can be obtained.

As used herein, "vector" refers to a DNA molecule such as a plasmid, cosmid, or bacterial phage for introducing a nucleotide construct, for example, an expression cassette, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance, or ampicillin resistance.

The methods of the invention involve introducing a polypeptide or polynucleotide into a plant. As used herein, "introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

A "stable transformation" is a transformation in which the nucleotide construct introduced into a plant integrates into the genome of the plant and is capable of being inherited by the progeny thereof. "Transient transformation" means that a polynucleotide is introduced into the plant and does not integrate into the genome of the plant or a polypeptide is introduced into a plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (Townsend, et al., U.S. Pat. No. 5,563,055 and Zhao, et al., U.S. Pat. No. 5,981,840), direct gene transfer (Paszkowski, et al., (1984) *EMBO J.* 3:2717-2722), and ballistic particle acceleration (see, for example, U.S. Pat. Nos. 4,945,050; 5,879,918; 5,886,244; 5,932,782; Tomes, et al., (1995) in Plant Cell, Tissue, and Organ Culture: Fundamental Methods, ed. Gamborg and Phillips (Springer-Verlag, Berlin); McCabe, et al., (1988) *Biotechnology* 6:923-926); and Lec1 transformation (WO 00/28058). Also see, Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in The Experimental Manipulation of Ovule Tissues, ed. Chapman, et al., (Longman, N.Y.), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford (1995) *Annals of Botany* 75:407-413 (rice); Osjoda, et al., (1996) *Nature Biotechnology* 14:745-750 (maize via *Agrobacterium tumefaciens*), all of which are herein incorporated by reference in their entirety.

In specific embodiments, the DNA constructs comprising the promoter sequences of the invention can be provided to a plant using a variety of transient transformation methods. Such transient transformation methods include, but are not limited to, viral vector systems and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. Methods for introducing polynucleotides into plants and expressing a protein encoded therein, involving viral DNA or RNA molecules, are known in the art. See, for example, U.S. Pat. Nos. 5,889,191, 5,889, 190, 5,866,785, 5,589,367, 5,316,931 and Porta, et al., (1996) *Molecular Biotechnology* 5:209-221, herein incorporated by reference in their entirety.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference in their entirety. Briefly, the polynucleotide of the invention can be contained in transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick, et al., (1986) *Plant Cell Reports* 5:81-84, herein incorporated by reference in its entirety. These plants may then be grown, and either pollinated with the same transformed strain or different strains, and the resulting progeny having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into its genome.

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, (1988) In: Methods for Plant Molecular Biology, (Eds.), Academic Press, Inc., San Diego, Calif., herein incorporated by reference in its entirety). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the embodiments containing a desired polynucleotide is cultivated using methods well known to one skilled in the art.

The embodiments provide compositions for screening compounds that modulate expression within plants. The vectors, cells, and plants can be used for screening candidate molecules for agonists and antagonists of the ADF4 promoter. For example, a reporter gene can be operably linked to an ADF4 promoter and expressed as a transgene in a plant. Compounds to be tested are added and reporter gene expression is measured to determine the effect on promoter activity.

The following examples are offered by way of illustration and not by way of limitation.

EXAMPLES

The embodiments are further defined in the following Examples, in which parts and percentages are by weight and degrees are Celsius, unless otherwise stated. It should be understood that these Examples, while indicating embodiments of the invention, are given by way of illustration only.

From the above discussion and these Examples, one skilled in the art can ascertain the essential characteristics of the embodiments, and without departing from the spirit and scope thereof, can make various changes and modifications of them to adapt to various usages and conditions. Thus, various modifications of the embodiments in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Identification of the ADF4 Gene

The actin depolymerization factor 4 (ADF4) gene was identified as a reproductive-tissue-preferred gene using Lynx Massively Parallel Signature Sequencing technology (MPSS™) (see, Brenner, et al., (2000) *Nature Biotechnology* 18:630-634, Brenner, et al., (2000) *Proc Natl Acad Sci USA* 97:1665-1670, herein incorporated by reference in its entirety).

The MPSS technology involves the generation of 17-base signature tags from mRNA samples that have been reverse transcribed. The tags are simultaneously sequenced and assigned to genes or ESTs. The abundance of these tags is given a number value that is normalized to parts per million (PPM) which then allows the tag expression, or tag abundance, to be compared across different tissues. Thus, the MPSS platform can be used to determine the expression pattern of a particular gene and its expression level in different tissues.

To characterize ADF4 gene expression, we surveyed across more than 250 experiments within the DuPont/Pioneer MPSS database. This database includes experiments from a range of tissue types, treatments, genotypes and developmental stages. Across all of these experiments, analysis revealed a high preference for reproductive tissue as summarized in FIG. 1. Primers were then designed to isolate the ADF4 promoter.

Example 2

Isolation of the ADF4 Promoter

Maize plants B73 were field grown in the summer of 2003 in Johnston, Iowa. Tissues from B73 were used for gene and promoter isolation. Promoter regions of the maize ADF4 gene were isolated from maize genomic DNA by amplifying the genomic DNA with the following oligonucleotide primers:

```
5'-AAGCTTGAGTGTTGTCGTGTTGCTCG      (SEQ ID NO: 2)

5'-CCATGGCCTTGAGCTCCAGGAACC        (SEQ ID NO: 3)
```

PCR was performed in a total volume of 50 uL using the High Fidelity PCR system from Roche (Basel) and 10 µmol of each primer as appropriate.

The full-length ADF4 promoter is disclosed in SEQ ID NO 1.

Example 3

Activity of the ADF4 Promoter and Fragments Thereof

To demonstrate that the DNA sequence isolated as the ADF4 promoter functions as a promoter, transgenic maize assays were performed. These assays provided a rapid assessment of whether the DNA sequence tested is able to direct gene expression.

The full length promoter (see, SEQ ID NO: 1) was PCR amplified from genomic DNA and cloned as a translational fusion with B-glucuronidase (GUS) and Red Fluorescent protein (RFP) and combined in a dual promoter cassette. Transgenic plants were created by transforming the dual promoter cassette into maize by *Agrobacterium* mediated transformation.

The transgenic maize plants were assayed for GUS and RFP expression. T0 and T1 transgenic plant material was analyzed for ADF4 promoter activity by excising plant tissues at a number of developmental stages. GUS expression was determined by immersing the excised plant tissues in either a GUS staining buffer (modified from Jefferson, et al., see, Jefferson (1987) *Plant Mol. Biol. Rep.* 5:387-405) containing 1.36 g $NaH_2PO_4$, 1.74 g $Na_2HPO_4$, 164 mg $K_4Fe(CN)_6 3H_2O$, 211 mg $K_3Fe(CN)_6$, 0.06 ml Triton X-100 and 50 mg X-Gluc (Sodium Salt) in a final volume of 100 ml, or a GUS staining buffer (McCabe, see. McCabe and Martinell (1993) *Bio/Technol.* 11:596-598) containing 1.36 g $NaH_2PO_4$, 1.74 g $Na_2HPO_4$, 16.4 mg $K_4Fe(CN)_6 3H_2O$, 0.29 g EDTA, 0.2 ml Triton X-100 and 50 mg X-Gluc (Sodium Salt) in a final volume of 100 ml. The plants were incubated in the dark overnight at 37° C. Replacing the GUS staining solution with 70% ethanol stopped the assay. GUS activity was visualized and pictures were taken. Red fluorescence protein was detected using a Nikon Eclipse E400 microscope with a red fluorescent protein filter.

Full Length Promoter (SEQ ID NO: 1) Analysis

Positive T0 events were identified, and plants containing the full length ADF4 promoter construct were stained in GUS solution for histochemical analysis. A control event was also tested. The positive events show very high activity in the immature ears compared to other tissues. (FIGS. 2-3).

Ten of the GUS-positive and RFP-positive events were advanced to a T1 generation and the GUS and RFP expression pattern were evaluated. Tissue was sampled from the following dates: week 1 (approximately V7-V8); week 2 (approximately V11); week 3 (approximately V14); week 4 (tasseling); week 5 (silking, not pollinated); week 6 (approximately one week after silking, not pollinated); week 7 (approximately 5-15 days after pollination); week 8 (approximately 15-20 days after pollination). The sampled events showed an immature ear-preferred expression pattern. (FIGS. 4A-4H).

This data is consistent with the expression pattern expected from the ADF4 promoter and confirms its reproductive-tissue-preferred expression pattern. The control events did not show any significant GUS staining.

Example 4

Identification of Regulatory Motifs in the ADF4 Promoter

Regulatory motifs of about six or eight bases within the ADF4 promoter sequence were identified by comparison to upstream sequences from orthologous genes from sorghum and rice using proprietary software as described in U.S. Patent Application Ser. No. 61/086,372. The 1000 base pairs upstream of the ADF4 promoter, relative to the ATG start of translation, were compared to the 1000 base pairs upstream sequence of the orthologous rice and sorghum genes. (FIG. 5). The comparison was performed through performing pairwise comparisons of multiple regulatory sequences from a plurality of orthologous species, here maize, rice and sorghum. The 300 base pair region shown in FIG. 3 is at position −253 to −553 relative to the translation start.

The regulatory motifs identified in Tables 1-3 were identified from comparison of ADF4 promoters from maize, sorghum and rice. FIG. 5 represents the corresponding bases to the motifs listed below.

TABLE 1

| | |
|---|---|
| 1 | TGGGCC |
| 2 | GTAGTAG |
| 3 | TCCCAC |
| 4 | TAGTAGT |
| 5 | ACATGAC |
| 6 | GAGAGAG |

TABLE 2

Promoter Elements matching with TGGGCC

| Promoter Element | Name | Function |
|---|---|---|
| CGAGGTGGGCCCGTAGGTGGGCCCGTAT | PCF, | meristematic tissue-specific element |
| GTGGGCCCG | GCBP2ZMGAPC4 | Binding site of tobacco nuclear factor (GCBP-2) found in the maize (Z.m.) GapC4 (Glyceraldehyde-3-phosphate dehydrogenase 4) gene promoter; Located between −293 and −285; See S000350; |
| TGGGCCCGT | SITEIIAOSPCNA | Site IIa of rice (O.s.) PCNA (proliferating cell nuclear antigen gene; Found at −197 to −188; Binding site for two nuclear proteins,PCF1 and PCF2 (Kosugi and Ohashi, 1997); nuclear proteins,involved in meristematic tissue-specific expression; Resemble thec onserved motif (T/GGTCCCAT) found in promoter regions of auxin-regulated genes; See S000026 (AUXREPSIAA4); |
| ATAATGGGCCACACTGTGGGGCAT (SEQ ID NO: 6) | SE1PVGRP18 | SE1 (Stem element 1) found in the bean (P.v.) grp1.8 gene promoter; Located between −121 and −94; Enhances the expression strongly but unspecifically; See S000289, S000101 (SE2); |

TABLE 3

Promoter Elements matching with TCCCAC

| Promoter Element | Name | Function |
| --- | --- | --- |
| CTCCCAC | BOXCPSAS1 | Box C in pea (P.s.) asparagine synthetase (AS1) gene; Found at −45; AS1 is negatively regulated by light;.@Box C binds with nuclear proteins, which was competed by a putative repressor element RE1 (see S000195); |
| TGGTCCCAC | SITEIIBOSPCNA | Site IIb of rice PCNA (proliferating cell nuclear antigen) gene; Found at −178 to −169; Binding site for two nuclear proteins, PCF1 and PCF2 (Kosugi and Ohashi, 1997); Suggested to be involved in meristematic tissue-specific expression; Resemble the conserved motif (T/GGTCCCAT) found in promoter regions of auxin-regulated genes; See S000026 (AUXREPSIAA4); |
| ATCCCACCTAC (SEQ ID NO: 7) | L box | part of a light responsive element |
| GATCCCACATACACATACACG (SEQ ID NO: 8) | napA, | seed storage protein, napA |

What is claimed is:

1. An isolated promoter consisting of the nucleotide sequence of positions 7-1026 of SEQ ID NO: 1 which is operably linked to a heterologous polynucleotide of interest, and wherein the promoter has reproductive tissue preferred promoter activity in a plant.

2. An expression cassette comprising the promoter of claim 1.

3. A vector comprising the expression cassette of claim 2.

4. A plant cell comprising the expression cassette of claim 2.

5. The plant cell of claim 4, wherein said expression cassette is stably integrated into the genome of the plant cell.

6. The plant cell of claim 4, wherein said plant cell is from a monocot.

7. The plant cell of claim 6, wherein said monocot is maize.

8. A plant comprising the expression cassette of claim 2.

9. The plant of claim 8, wherein said plant is a monocot.

10. The plant of claim 9, wherein said monocot is maize.

11. The plant of claim 8, wherein said expression cassette is stably incorporated into the genome of the plant.

12. A transgenic seed of the plant of claim 11, wherein the transgenic seed comprises the expression cassette.

13. The plant of claim 8, wherein the heterologous polynucleotide of interest encodes a gene product that confers drought tolerance, cold tolerance, herbicide tolerance, pathogen resistance, or insect resistance.

14. The plant of claim 8, wherein expression of said heterologous polynucleotide of interest alters a phenotype of said plant.

* * * * *